(12) United States Patent
Ford et al.

(10) Patent No.: US 7,576,212 B2
(45) Date of Patent: Aug. 18, 2009

(54) THIENO[2,3-B] PYRIDINES AS POTASSIUM CHANNEL INHIBITORS

(75) Inventors: John Ford, Huntingdon (GB); Nicholas John Palmer, Cambridge (GB); John Frederick Atherall, Essex (GB); David John Madge, Cambridgeshire (GB); Derek John, Cambridgeshire (GB)

(73) Assignee: Xention Limited, Pampisford, Cambridge (GB)

( * ) Notice: Subject to any disclaimer, the term of this patent is extended or adjusted under 35 U.S.C. 154(b) by 315 days.

(21) Appl. No.: 11/297,330

(22) Filed: Dec. 9, 2005

(65) Prior Publication Data

US 2006/0183768 A1    Aug. 17, 2006

Related U.S. Application Data

(60) Provisional application No. 60/634,271, filed on Dec. 9, 2004.

(51) Int. Cl.
C07D 513/02        (2006.01)
(52) U.S. Cl. .................................................. 546/114
(58) Field of Classification Search .................. 546/114
See application file for complete search history.

(56) References Cited

U.S. PATENT DOCUMENTS

| | | | |
|---|---|---|---|
| 3,845,065 A | 10/1974 | Shen et al. | |
| 3,903,095 A | 9/1975 | Shen et al. | |
| 4,146,716 A | 3/1979 | Cox et al. | |
| 4,165,374 A | 8/1979 | Troxler et al. | |
| 6,184,221 B1 | 2/2001 | Gerlach et al. | |
| 6,521,618 B2 | 2/2003 | Boschelli et al. | |
| 6,531,495 B1 | 3/2003 | Brendel et al. | |
| 2002/0161011 A1 | 10/2002 | Beaudoin et al. | |
| 2003/0027829 A1 | 2/2003 | Reed et al. | |
| 2004/0097485 A1 | 5/2004 | Burkitt et al. | |
| 2005/0026935 A1 | 2/2005 | Ford et al. | |
| 2005/0282829 A1 | 12/2005 | Ford et al. | |
| 2007/0161672 A1 | 7/2007 | Ford et al. | |

FOREIGN PATENT DOCUMENTS

| | | | |
|---|---|---|---|
| AU | 521790 | | 11/1979 |
| DE | 1965710 A1 | | 7/1970 |
| DE | 28 31 677 A1 | | 2/1979 |
| DE | 226 893 A1 | | 9/1985 |
| DE | 248 593 A1 | | 8/1987 |
| DE | 101 04 802 A1 | | 8/2002 |
| GB | 1284930 | | 8/1972 |
| GB | 1 570 494 | | 7/1980 |
| GB | EP 126970 | * | 4/1984 |
| JP | 48-81892 | | 11/1973 |
| JP | 48-81893 | | 11/1973 |
| JP | 3254843 | * | 2/1995 |
| JP | 07-076586 | | 3/1995 |
| JP | 07076586 | * | 3/1995 |
| RU | 2 116 309 C1 | | 7/1998 |
| WO | WO 98/04521 A1 | | 2/1998 |
| WO | WO 98/04542 A1 | | 2/1998 |
| WO | WO 98/18475 A1 | | 5/1998 |
| WO | WO 98/18476 A1 | | 5/1998 |
| WO | WO 99/37607 A1 | | 7/1999 |
| WO | WO 99/62891 A1 | | 12/1999 |
| WO | WO 00/12492 A1 | | 3/2000 |
| WO | WO 00/25774 A1 | | 5/2000 |
| WO | WO 01/00573 A1 | | 1/2001 |
| WO | WO 01/21609 A1 | | 3/2001 |
| WO | WO 01/21610 A1 | | 3/2001 |
| WO | WO 01/25189 A1 | | 4/2001 |

(Continued)

OTHER PUBLICATIONS

Shvedov et al, STN Accession No. 1974:95865 Document No. 80:95865, Abstract of Khimiya Geterotsiklicheskikh Soedinenii (1974), (1), 58-60.*

(Continued)

Primary Examiner—D. Margaret Seaman
Assistant Examiner—Nizal S Chandrakumar
(74) Attorney, Agent, or Firm—Sterne, Kessler, Goldstein & Fox P.L.L.C.

(57) ABSTRACT

The invention provides compounds of the formula:

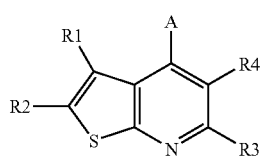

wherein
R1 is aryl, heteroaryl, cycloalkyl or alkyl;
R2 is H, alkyl, nitro, $CO_2R7$, $CONR5R6$ or halo;
R3 and R4 are H, $NR5R6$, $NC(O)R7$, halo, trifluromethyl, alkyl, $CONR5R6$, $CO_2R7$, nitrile or alkoxy;
R5 and R6 may be the same or different and may be H, alkyl, aryl, heteroaryl or cycloalkyl; or R5 and R6 may together form a saturated, unsaturated or partially saturated 4 to 7 member ring, wherein said ring may optionally comprise one or more further heteroatoms selected from N, O or S;
R7 is H or alkyl;
A is H, halo, or a group of formula X-L-Y;
X is O, S or NR8;
R8 is H or alkyl;
L is $(CH_2)_n$, where n is 0, 1, 2, 3 or 4; and
Y is aryl, a heterocyclic group, alkyl, alkenyl or cycloalkyl;
the products of mono- and di-oxidation of sulphur and/or mono-oxidation of nitrogen moieties in compounds of formula I;
or a pharmaceutically acceptable salt thereof.

These compounds find use as inhibitors of potassium ion channels and thus are useful in the treatment of various conditions including arrhythmia and type-2 diabetes mellitus.

10 Claims, No Drawings

FOREIGN PATENT DOCUMENTS

| WO | WO 01/25224 A1 | 4/2001 |
|---|---|---|
| WO | WO 01/27107 A2 | 4/2001 |
| WO | WO 01/40231 A1 | 6/2001 |
| WO | WO 01/46155 A1 | 6/2001 |
| WO | WO 02/24655 A1 | 3/2002 |
| WO | WO 02/36556 A2 | 5/2002 |
| WO | WO 02/44137 A1 | 6/2002 |
| WO | WO 02/46162 A1 | 6/2002 |
| WO | WO 02/48131 A1 | 6/2002 |
| WO | WO 02/060874 A1 | 8/2002 |
| WO | WO 02/064581 A1 | 8/2002 |
| WO | WO 02/087568 A1 | 11/2002 |
| WO | WO 02/088073 A1 | 11/2002 |
| WO | WO 02/100825 A2 | 12/2002 |
| WO | WO 03/000675 A1 | 1/2003 |
| WO | WO 03/063797 A2 | 8/2003 |
| WO | WO 2004/092123 A2 | 10/2004 |
| WO | WO 2004/111057 A1 | 12/2004 |
| WO | WO 2005/105809 A1 | 11/2005 |
| WO | WO 2006/106326 A1 | 10/2006 |
| WO | WO 2007/066127 A2 | 6/2007 |

OTHER PUBLICATIONS

Klemm et al. STN Accession No. 1974:491385 Document No. 81:91385 Abstract Journal of Heterocyclic Chemistry (1974), 11(3), 355-61.*
Pedersen et al. STN Accession No. 1978:50683 Document No. 88:50683 Abstract Tetrahedron (1977), 33(16), 2089-92.*
Harb et al. STN Accession No. 1992:255564 Document No. 116:255564 Abstract Bulletin of the Faculty of Science, Assiut University (1991), 20(2), 55-63.*
Klemm, L.H., et al., "Chemistry of Thienopyridines. VIII. Substitution Products Derived from Thieno [2,3-*b*] pyridine 7-Oxide (1)," *J. Heterocycl. Chem. 7*:81-89, Journal of Heterocyclic Chemistry (1970).
Klemm, L.H., and Merrill, R.E., "Chemistry of Thienopyridines. XIII. Selective Formation of Sulfones in Bi- and Tricyclic Systems. Thieno [2,3-*b*] pyridine 1,1-Dioxide as a Dienophile (1)," *J. Heterocycl. Chem. 9*:293-298, Journal of Heterocyclic Chemistry (1972).
Klemm, L.H., and Merrill, R.E., "Chemistry of Thienopyridines. XVIII. Lithiation as a Route to 2- and 3-Substituted Thieno [2,3-*b*)pyridines (1)," *J. Heterocycl. Chem. 7*:355-361, Journal of Heterocyclic Chemistry (1974).
Klemm, L.H., and Hartling, R., "Chemistry of Thienopyridines. XXIV. Two Transformations of Thieno [2,3-*b*] pyridine 7-Oxide (1)," *J. Heterocyclic Chem. 13*:1197-1200, Journal of Heterocyclic Chemistry (1976).
Pedersen, E.B., and Carlsen, D., "Phosphoramides-V. Synthesis of 4,6-Bis(Dimethylamino)Thieno[2,3-b]Pyridines by an HMPT Induced Ring Closure Reaction," *Tetrahedron 33*:2089-2092, Pregamon Press (1977).
Sabnis, R.W., "The Gewald Synthesis," *Sulfur Reports 16*:1-17, Hardwood Academic Publishers GmbH (1994).
Schäfer, H., et al., "2-Arylamino-thiophen-3-carbonsäurederivate," *J. F. Prakt. Chemie 326*:917-928, Johan Ambrosius Barth Leipzig (1984).
Gewald reaction, Wikipedia, http://en.wikipedia.org/wiki/Gewald_reaction, 2 pages, accessed on Aug. 22, 2008.
Amos, G.J., et al., "Differences between outward currents of human atrial and subepicardial ventricular myocytes," *J. Physiol. 491*:31-50, Cambridge Univ. Press. (1996).
Armstrong, C.M. and Hille, B., "Voltage-Gated Ion Channels and Electrical Excitability," *Neuron 20*:371-380, Cell Press (1998).
Bachmann, A., et al., "Characterization of a novel Kv1.5 channel blocker in Xenopus oocytes, CHO cells, human and rat cardiomyocytes," *Naunyn-Schmiedeberg's Arch. Pharmacol. 364*:472-478, Springer-Verlag (2001).
Belen'kii, L.I., et al., "Synthesis of Heterocyclic Compounds from the Products of Addition of Polyhaloalkanes to Unsaturated Systems.

4. Synthesis of Substituted Furo[2,3-D]Pyrimidines," *Chemistry of Heterocyclic Compounds 29*:109-114, Plenum Publishing Corporation (1993).
Brendel, J. and Peukert, S., "Blockers of the Kv1.5 channel for the treatment of atrial arrhythmias," *Expert Opin. Ther. Patents 12*:1589-1598, Ashley Publications Ltd. (2002).
Campaigne, E., "Thiophenes and their Benzo Derivatives: (iii) Synthesis and Applications," in *Comprehensive Heterocyclic Chemistry: The Structure, Reactions, Synthesis and Uses of Heterocyclic Compounds 4*, Bird, C.W., et al., eds., Pergamon Press, New York, NY, pp. 863-934 (1984).
Colatsky, T.J., et al., "Channel Specificity in Antiarrhythmic Drug Action: Mechanism of Potassium Channel Block and Its Role in Suppressing and Aggravating Cardiac Arrhythmias," *Circulation 82*:2235-2242, American Heart Association (1990).
Courtemanche, M., et al., "Ionic targets for drug therapy and atrial fibrillation-induced electrical remodeling: insights from a mathematical model," *Cardiovasc. Res. 42*:477-489, Elsevier Science B.V. (1999).
Fedida, D., et al., "Identity of a Novel Delayed Rectifier Current From Human Heart With a Cloned $K^+$ Channel Current," *Circ. Res. 73*:210-216, Lippincott Williams & Wilkins (1993).
Feng, J., et al., "Antisense Oligodeoxynucleotides Directed Against Kv1.5 mRNA Specifically Inhibit Ultrarapid Delayed Rectifier $K^+$ Current in Cultured Adult Human Atrial Myocytes," *Circ. Res. 80*:572-579, American Heart Association, Inc. (1997).
Feng, J., et al., "Effects of Class III Antiarrhythmic Drugs on Treatment Outward and Ultra-rapid Delayed Rectifier Currents in Human Atrial Myocytes," *J. Pharmacol. Exp. Ther. 281*:384-392, American Society for Pharmacology and Experimental Therapeutics (1997).
Ford, J.W., et al., "Potassium Channels: Gene Family, Therapeutic Relevance, High-Throughput Screening Technologies and Drug Discovery," in *Progress in Drug Research*, vol. 58, Jucker, E., ed., Birkhäuser Verlag, Boston, MA, pp. 133-168 (2002).
Godreau, D., et al., "Mechanisms of Action if Antiarrhythmic Agent Bertosamil on hKv1.5 Channels and Outward Potassium Current in Human Atrial Myocytes," *J. Pharmacol. Exp. Ther. 300*:612-620, American Society for Pharmacology and Experimental Therapeutics (2002).
Gutman, G.A., et al., "International Union of Pharmacology. XLI. Compendium of Voltage-Gated Ion Channels: Potassium Channels," *Pharmacol. Rev. 55*:583-586, American Society for Pharmacology and Experimental Therapeutics (Dec. 2003).
Hebert, S.C., "General Principles of the Structure of Ion Channels," *Am. J. Med. 104*:87-98, Excerpta Medica, Inc. (1998).
Hosni, H.M., et al., "Thienopyrimidines II: Synthesis of Newer Thieno[2,3-d]-Pyrimidines and Their Quaternized Derivatives with Molluscicidal Activity," *Acta Pol. Pharm.—Drug Res. 56*:49-56, Polish Pharmaceutical Society (1999).
Hozien, Z.A., et al., "Synthesis and Application of Some New Thienopyrimidine Dervatives as Antimicrobial Agents," *Synthetic Communications 26*:3733-3755, Marcel Dekker, Inc. (1996).
Ismail, K.A., et al., "Synthesis and Antimicrobial Activity of Some Tetramethylenethieno[2,3-d]pyrimidine derivatives," *Il Farmaco 50*:611-616, Elsevier (1995).
Jordis, U., et al., "7,9-Dideaza-9-Thiaadenines (4-Aminothieno/2,3-d/pyrimidines) as Potential Anticytokinines," *Vestn. Slov. Kem. Drus. 33*:217-238, Drustvo (1986).
Katada, J., et al., "Cytotoxic effects of NSL-1406, a new thienopyrimidine derivative, on leukocytes and osteoclasts," *Bioorg. Med. Chem. Lett. 9*:797-802, Elsevier Science Ltd. (1999).
Knobloch, K., et al., "Electrophysiological and antiarrhythmic effects of the novel $I_{Kur}$ channel blockers, S9947 and S20951, on left vs. right pig atrium in vivo in comparison with the $I_{Kr}$ blockers dofetilide, azimilide, d,l-sotalol and ibutilide," *Naunyn-Schmiedeberg's Arch. Pharmacol. 366*:482-487, Springer-Verlag (2002).
Konno, S., et al., "Synthesis of Thienopyrimidine Derivatives and Their Antifungal Activities," *Yakugaku Zasshi 109*:464-473, Pharmaceutical Society of Japan (1989).
Li, G.-R., et al., "Evidence for Two Components of Delayed Rectifier $K^+$ Current in Human Ventricular Myocytes," *Circ. Res. 78*:689-696, American Heart Association, Inc. (1996).

Malayev, A.A., et al., "Mechanism of Clofilium Block of the Human Kv1.5 Delayed Recitifer Potassium Channel," *Mol. Pharmacol. 47*:198-205, American Society for Pharmacology and Experimental Therapeutics (1995).

Marbán, E., "Cardiac channelopathies," *Nature 415*:213-218, Macmillan Magazines Ltd. (2002).

Matsuda, T., et al., "Inhibition by a novel anti-arrhythmic agent, NIP-142, of cloned human cardiac $K^+$ channel Kv1.5 current," *Life Sci. 68*:2017-2024, Elsevier Science, Inc. (2001).

Moneer, A.A., et al., "Reaction of 3-Amino and 4-hydrazino-5,6-Tetramethylenethieno[2,3-d]Pyrimidine Derivatives with Azlactones," *Egypt. J. Pharm. Sci. 34*:599-609, National Information & Documentation Centre (1993).

Munchhof, M.J., et al., "Design and SAR of thienopyrimidine and thienopyridine inhibitors of VEGFR-2 kinase activity," *Bioorg. Med. Chem. Lett. 14*:21-24, Elsevier Ltd. (Jan. 2004).

Nakayama, J., "Thiophenes and their Benzo Derivatives: Synthesis," in *Comprehensive Heterocyclic Chemistry II*, vol. 2: Katritzky, A.R., et al., eds., pp. 607-677, Pergamon Press, New York, NY (1996).

Nattel, S., et al., "Cardiac Ultrarapid Delayed Rectifiers: A Novel Potassium Current Family of Functional Similarity and Molecular Diversity," *Cell Physiol. Biochem. 9*:217-226, S. Karger AG (1999).

Nattel, S., "Therapeutic implications of atrial fibrillation mechanisms: can mechanistic insights be used to improve AF management?," *Cardiovasc. Res. 54*:347-360, Elsevier Science B.V. (2002).

Noravyan, A.S., et al., "Synthesis and anticonvulsive activity of 4-alkyl (or aryl)amino-6,6-dimethyl-5,6-dihydro-8H-pyrano (or thiopyrano)[3,4-b]thieno[5,4-d] pyrimidines," *Khimiko-Farmatsevticheskii Zhurnal 11*:38-42, Folium Publishing Company (1977).

Peukert, S., et al., "Identification, Synthesis, and Activity of Novel Blockers of the Voltage-Gated Potassium Channel Kv1.5," *J. Med. Chem. 46*:486-498, American Chemical Society (Feb. 2003).

Ram, V.J., "Thieno[2,3-*d*]pyrimidines as Potential Chemotherapeutic Agents," *Arch. Pharm. (Weinheim) 312*:19-25, Verlag Chemie, GmbH (1979).

Ram, V.J., et al., "Thieno[2,3-*d*]pyrimidines as Potential Chemotherapeutic Agents. II," *J. Heterocyclic Chem. 18*:1277-1280, HeteroCorporation (1981).

Shehata, I.A., et al., "Synthesis, Antitumor and Anti-HIV-1 Testing of Certain Thieno[2,3-*d*]pyrimidine, Thieno[2,3-*d*]imidazo[1,2-*c*]pyrimidine and Thieno[2,3-*d*][1,3]thiazine Derivatives," *Med. Chem. Res. 6*:148-163, Birkhäuser Boston (1996).

Shieh, C.-C., et al., "Potassium Channels: Molecular Defects, Diseases, and Therapeutic Opportunities," *Pharmacol. Rev. 52*:557-593, American Society for Pharmacology and Experimental Therapeutics (2000).

Stewart, A.O., et al., "Discovery of Inhibitors of Cell Adhesion Molecule Expression in Human Endothelial Cells. 1. Selective Inhibition of ICAM-1 and E-Selectin Expression," *J. Med. Chem. 44*:988-1002, American Chemical Society (2001).

Tyle, P., "Iontophoretic Devices for Drug Delivery," *Pharm. Res. 3*:318-326, Plenum Publishing Corporation (1986).

Wang, Z., et al., "Sustained Depolarization-Induced Outward Current in Human Atrial Myocytes: Evidence for a Novel Delayed Rectifier $K^+$ Current Similar to Kv1.5 Cloned Channel Currents," *Circ. Res. 73*:1061-1076, American Heart Association (1993).

Wang, Z., et al., "Effects of Flecainide, Quinidine, and 4-Aminopyridine on Transient Outward and Ultrarapid Delayed Rectifier Currents in Human Atrial Myocytes," *J. Pharmacol. Exp. Ther. 272*:184-196 (1995).

Wirth, K.J., et al., "Atrial effects of the novel $K^+$-channel-blockers AVE0118 in anesthetized pigs," *Cardiovasc. Res. 60*:298-306, Elsevier B.V. (Nov. 2003).

Xu, D.H. and Xu, S.B., "The Expression of Arrhythmic Related Genes on *Xenopus* Oocytes for Evaluation of Class III Antiarrhythmic Drugs from Ocean Active Material," *Acta Genetica Sinica 27*:195-201, Science Press and Elsevier Press (2000).

Dialog File 351, Accession No. 607591, Derwent WPI English language abstract for JP 48-81892 (listed on accompanying PTO/SB/08A as document FP1).

Dialog File 351, Accession No. 607592, Derwent WPI English language abstract for JP 48-81893 (listed on accompanying PTO/SB/08A as document FP2).

Dialog File 351, Accession No. 3566123, Derwent WPI English language abstract for DD 226 893 A1 (listed on accompanying PTO/SB/08A as document FP10).

Dialog File 351, Accession No. 12964595, Derwent WPI English language abstract for DE 101 04 802 A1 (listed on accompanying PTO/SB/08A as document FP23).

Co-pending U.S. Appl. No. 11/635,786, inventors Ford, J., et al., filed Dec. 8, 2006 (Not Published).

STNEasy Database, Accession No. 1978:37739, English language abstract for Noravyan, A.S., et al., "Synthesis and anticonvulsive activity of 4-alkyl (or aryl)amino-6,6-dimethyl-5,6-dihydro-8H-pyrano (or thiopyrano)[3,4-b]thieno[5,4-d] pyrimidines," *Khimiko-Farmatsevticheskii Zhurnal 11*:38-42, Folium Publishing Company (1977).

Abdelrazek, F.M., et al., "Synthesis of Novel Thieno[2,3-*d*]pyrimidine, Thieno[2,3-*b*]pyridine and Thiazolo[3,2-*a*]thieno[2,3-*d*]pyrimidine Derivatives and their effect on the production of Mycotoxins," *Arch. Pharm. (Weinheim) 325*:301-306, VCH Verlagsgesellschaft mbH (1992).

Baell, J.B., et al., "Khellinone Derivatives as Blockers of the Voltage-Gated Potassium Channel Kv1.3: Synthesis and Immunosuppressive Activity," *J. Med. Chem. 47*:2326-2336, American Chemical Society (Apr. 2004).

Barker, J.M., et al., "Thienopyridines. Part 6. Synthesis and Nucleophilic Substitution of Some Chlorothieno[2,3-b]pyridine Derivatives, and Comparisons with the Analogous Quinoline Compounds," *J. Chem. Research (M)*:2501-2523, Science Reviews, Ltd. (1985).

Beeton, C., et al., "Selective blockade of T lymphocyte $K^+$ channels ameliorates experimental autoimmune encephalomyelitis, a model for multiple sclerosis," *Proc. Natl. Acad. Sci. USA 98*:13942-13947, National Academy of Sciences (2001).

Beeton, C., et al., "A Novel Fluorescent Toxin to Detect and Investigate Kv1.3 Channel Up-regulation in Chronically Activated T Lymphocytes," *J. Biol. Chem. 278*:9928-9937, American Society for Biochemistry and Molecular Biology, Inc. (Mar. 2003).

Boschelli, D.H., et al., "Identification of 7-Phenylaminothieno-[3,2-*b*]pyridine-6-carbonitriles as a New Class of Src Kinase Inhibitors," *J. Med. Chem. 47*:6666-6668, American Chemical Society (Dec. 2004).

Charvát, T., et al., "Diethyl Acetonedicarboxylate—a Precursor for the Synthesis of New Substituted 4-Aminoquinolines and Fused 4-Aminopyridines," *Monatshefte für Chemie 126*:333-340, Springer-Verlag (1995).

Desir, G.V., "Kv1.3 potassium channel blockade as an approach to insulin resistance," *Expert Opin. Ther. Targets 9*:571-579, Ashley Publications Ltd. (Jun. 2005).

Felix, J.P., et al., "Identification and Biochemical Characterization of a Novel Nortriterpene Inhibitor of the Human Lymphocyte Voltage-Gated Potassium Channel, Kv1.3," *Biochemistry 38*:4922-4930, American Chemical Society (1999).

Friedrich, M., et al., "Flow cytometric characterization of lesional T cells in psoriasis: intracellular cytokine and surface antigen expression indicates an activated, memory/effector type 1 immunophenotype," *Arch. Dermatol. Res. 292*:519-521, Springer-Verlag (2000).

Gewald, K., et al., "Synthesen von 4-Amino-thieno[2,3-*b*]pyridinen," *Monatshefte für Chemie 110*:1189-1196, Springer-Verlag (1979).

Gilis, P.M., et al., "Synthesis and antibacterial evaluation of 4,7-dihydro-4-oxothieno[2,3-b] pyridine-5-carboxylic acids," *Eur. J. Med. Chem. Chim. Ther. 13*:265-269, Editions Scientifiques Elsevier (1978).

Hanson, D.C., et al., "UK-78,282, a novel piperidine compound that potently blocks the Kv1.3 voltage-gated potassium channel and inhibits human T cell activation," *Br. J. Pharmacol. 126*:1707-1716, Stockton Press (1999).

Leonard, R.J., et al., "Selective blockers of voltage gated $K^+$ channels depolarize human T lymphocytes: Mechanism of the antiproliferative effect of charybdotoxin," *Proc. Natl. Acad. Sci. USA* 89:10094-10098, National Academy of Sciences (1992).

Marco, J.L., et al., "Synthesis and Acetylcholinesterase/Butyrylcholinesterase Inhibition Activity of 4-Amino-2,3-diaryl-5,6,7,8-tetrahydrofuro(and thieno)[2,3-*b*]-quinolines, and 4-Amino-5,6,7,8,9-pentahydro-2,3-diphenylcyclohepta[*e*]furo(and thieno)-[2,3-*b*] pyridines," *Arch. Pharm. Pharm. Med. Chem.* 335:347-353, Wiley-VCH GmbH & Co. (2002).

Meadows, H.J., et al., "Effect of SB-205384 on the decay of GABA-activated chloride currents in granule cells cultured from rat cerebellum," *Br. J. Pharmacol.* 121:1334-1338, Stockton Press (1997).

Nguyen, A., et al., "Novel Nonpeptide Agents Potently Block the C-Type Inactivated Conformation of Kv1.3 and Suppress T Cell Activation," *Mol. Pharmacol.* 50:1672-1679, American Society for Pharmacology and Experimental Therapeutics (1996).

O'Connor, K.C., et al., "The Neuroimmunology of Multiple Sclerosis: Possible Roles of T and B Lymphocytes in Immunopathogenesis," *J. Clin. Immunol.* 21:81-92, Plenum Publishing Corporation (2001).

Page, R.L. and Roden, D.M., "Drug Therapy for Atrial Fibrillation: Where Do We Go from Here?," *Nat. Rev. Drug Discov.* 4:899-910, Nature Publishing Group (Nov. 2005).

Schmitz, A., et al., "Design of PAP-1, a Selective Small Molecular Kv1.3 Blocker, for the Suppression of Effector Memory T Cells in Autoimmune Diseases," *Mol. Pharmacol.* 68:1254-1270, American Society for Pharmacology and Experimental Therapeutics (Nov. 2005).

Shah, K., et al., "Immunosuppressive effects of a Kv1.3 inhibitor," *Cell. Immunol.* 221:100-106, Elsevier Science (Feb. 2003).

Suzuki, M., et al., "Synthesis and Biological Evaluations of Condensed Pyridine and Condensed Pyrimidine-Based HMG-CoA Reductase Inhibitors," *Bioorg. Med. Chem. Lett.* 11:1285-1288, Elsevier Science Ltd (2001).

Valverde, P., et al., "Potassium Channel-blockers as Therapeutic Agents to Interfere with Bone Resorption of Periodontal Disease," *J. Dent. Res.* 84:488-499, International & American Associations for Dental Research (Jun. 2005).

Vennekamp, J., et al., "Kv1.3-Blocking 5-Phenylalkoxypsoralens: A New Class for Immunomodulators," *Mol. Pharmacol.* 65:1364-1374, American Society for Pharmacology and Experimental Therapeutics (Jun. 2004).

Viglietta, V., et al., "GAD65-reactive T cells are activated in patients with autoimmune type la diabetes," *J. Clin. Invest.* 109:895-903, American Society for Clinical Investigation (2002).

Wulff, H., et al., "Alkoxypsoralens, Novle Nonpeptide Blockers of *Shaker*-Type K$^+$ Channels: Synthesis and Photoreactivity," *J. Med. Chem.* 41:4542-4549, American Chemical Society (1998).

Wulff, H., et al., "Potassium channels as therapeutic targets for autoimmune disorders," *Curr. Opin. Drug Discov. Devel.* 6:640-647, Thomson Scientific (Sep. 2003).

Wulff, H., et al., "The voltage-gated Kv1.3 K$^+$ Channel in effector memory T cells as new targets for MS," *J. Clin. Invest.* 111:1703-1713, American Society for Clinical Investigation (Jun. 2003).

Wulff, H., et al., "K$^+$ Channel Expression during B Cell Differentiation: Implications for Immunomodulation and Autoimmunity," *J. Immunol.* 173:776-786, American Association of Immunologists, Inc. (Jul. 2004).

Xu, J., et al., "The voltage-gated potassium channel Kv1.3 regulates peripheral insulin sensitivity," *Proc. Natl. Acad. Sci. USA* 101:3112-3117, National Academy of Sciences (Mar. 2004).

Yamashita, K., et al., "Severe chronic graft-versus host disease is characterized by a preponderance to CD4$^+$ effector memory cells relative to central memory cells," *Blood* 103:3986-3988, American Society of Hematology (May 2004).

Yoon, J.-W. and Jun, H.-S., "Cellular and Molecular Pathogenic Mechanisms of Insulin-Dependent Diabetes Mellitus," *Ann. NY Acad. Sci.* 928:200-211, New York Academy of Sciences (2001).

International Search Report for International Application No. PCT/GB2004/002454, European Patent Office, Netherlands, mailed on Nov. 2, 2004.

Dialog File 351, Accession No. 197029, Derwent WPI English language abstract for DE 1965710 (listed on the accompanying PTO/SB/08a form as document FP36).

Dialog File 351, Accession No. 1689342, Derwent WPI English language abstract for DE 28 31 677 A1 (listed on the accompanying PTO/SB/08a form as document FP37).

English-language abstract for Japanese Application Publication JP 3254843 (listed on the accompanying PTO/SB/08a form as document FP39).

English-language abstract for Japanese Application Publication JP 07-076586 (listed on the accompanying PTO/SB/08a form as document 40).

Feit, P.W. And Nielsen, O.B.T., "Aminobenzoic Acid Diureteics. 3,4-Disubstituted 5-Methylsulfonylbenzoic Acids and Related Compounds," *J. Med. Chem.* 19:402-406, American Chemical Society (1976).

International Search Report for International Patent Application No. PCT/GB2004/002454, European Patent Office, Netherlands, mailed Nov. 2, 2004.

International Search Report for International Patent Application No. PCT/GB2005/004753, European Patent Office, Netherlands, mailed Mar. 22, 2006.

Molina, P. et al., "An Efficient Iminophosphorane-Mediated Synthesis of Thieno[3,2-c]pyridine, Thieno[2,3-c]pyridine and Furo[3,2-c]-pyridine Derivatives," *Synthesis* 1:45-48, Thieme Chemistry (1987).

Moore, S., Office Action for U.S. Appl. No. 10/864,771, filed Jun. 10, 2004, U.S. Patent and Trademark Office, Alexandria, Virginia, mailed Feb. 4, 2009.

Moore, S., Advisory Action for U.S. Appl. No. 10/864,771, filed Jun. 10, 2004, U.S. Patent and Trademark Office, Alexandria, Virginia, mailed Aug. 1, 2009.

Moore, S., Office Action for U.S. Appl. No. 10/864,771, filed Jun. 10, 2004, U.S. Patent and Trademark Office, Alexandria, Virginia, mailed Jan. 23, 2008.

Moore, S., Interview Summary for U.S. Appl. No. 10/864,771, filed Jun. 10, 2004, U.S. Patent and Trademark Office, Alexandria, Virginia, mailed Jan. 10, 2008.

Moore, S., Office Action for U.S. Appl. No. 10/864,771, filed Jun. 10, 2004, U.S. Patent and Trademark Office, Alexandria, Virginia, mailed Apr. 5, 2007.

O'Dell, D.K., Office Action for U.S. Appl. No. 11/635,786, filed Dec. 8, 2006, U.S. Patent and Trademark Office, Alexandria, Virginia, mailed Dec. 22, 2008.

Pantani, G.A. and LaVoie, E.J., "Bioisosterism: A Rational Approach in Drug Design," *Chem. Rev.* 96:3147-3176, American Chemical Society (1996).

\* cited by examiner

THIENO[2,3-B] PYRIDINES AS POTASSIUM CHANNEL INHIBITORS

CROSS REFERENCE TO RELATED APPLICATIONS

This application claims the benefit of U.S. Provisional Application No. 60/634,271, filed Dec. 9, 2004, which is herein incorporated by reference herein.

BACKGROUND OF THE INVENTION

The present invention relates to thienopyridine compounds which are potassium channel inhibitors. Pharmaceutical compositions comprising the compounds and their use in the treatment of arrhythmia, type-2 diabetes mellitus, immunological disorders, including rheumatoid arthritis, type-1 diabetes, inflammatory bowel disorder and demyelinating disorders such as multiple sclerosis are also provided.

Ion channels are proteins that span the lipid bilayer of the cell membrane and provide an aqueous pathway through which specific ions such as $Na^+$, $K^+$, $Ca^{2+}$ and $Cl^-$ can pass (Herbert, 1998). Potassium channels represent the largest and most diverse sub-group of ion channels and they play a central role in regulating the membrane potential and controlling cellular excitability (Armstrong & Hille, 1998). Potassium channels have been categorized into gene families based on their amino acid sequence and their biophysical properties (for nomenclature see Gutman et al., 2003).

Compounds which modulate potassium channels have multiple therapeutic applications in several disease areas including cardiovascular, neuronal, auditory, renal, metabolic and cell proliferation (Shieh et al., 2000; Ford et al., 2002). More specifically potassium channels such as Kv4.3, Kir2.1, hERG, KCNQ1/minK, IKACh, IKAdo, $K_{ATP}$ and Kv1.5 are involved in the repolarisation phase of the action potential in cardiac myocytes. These potassium channels subtypes have been associated with cardiovascular diseases and disorders including long QT syndrome, hypertrophy, ventricular fibrillation, and atrial fibrillation, all of which can cause cardiac failure and fatality (Marban, 2002).

The human delayed rectifier voltage gated potassium channel subunit, Kv1.5, is exclusively expressed in atrial myocytes and is believed to offer therapeutic opportunities for the management of atrial fibrillation for several different reasons (see review of Brendel and Peukert, 2002): (i) There is evidence that Kv1.5 underlies the cardiac ultrarapid delayed rectifier ($KV_{(ur)}$) physiological current in humans due to similar biophysical and pharmacological properties (Wang et al., 1993; and Fedida et al., 1993). This has been supported with antisense oligonucleotides to Kv1.5 which have been shown to reduce $Kv_{(ur)}$ amplitude in human atrial myocytes (Feng et al., 1997). (ii) electrophysiological recordings have demonstrated that $KV_{(ur)}$ is selectively expressed in atrial myocytes, and therefore avoids inducing potentially fatal ventricular arrhythmia through interfering with ventricular repolarisation (Amos et al., 1996; Li et al., 1996; and Nattel, 2002). (iii) Inhibiting $Kv_{(ur)}$ in atrial fibrillation-type human atrial myocytes prolonged the action potential duration compared to normal healthy human atrial myocytes (Courtemanche et al., 1999). (iv) Prolonging the action potential duration by selectively inhibiting Kv1.5 could present safer pharmacological interventions for protecting against atrial re-entrant arrhythmias such as atrial fibrillation and atrial flutter compared to traditional class III antiarrythmics, by prolonging the atrial refractory period while leaving ventricular refractoriness unaltered (Nattel et al., 1999, Knobloch et al., 2002; and Wirth et al., 2003). Class III antiarrythmics have been widely reported as a preferred method for treating cardiac arrhythmias (Colatsky et al., 1990).

Drugs that maintain the sinus rhythm long-term without proarrhythmic or other side effects are highly desirable and not currently available. Traditional and novel class III antiarrythmic potassium channel blockers have been reported to have a mechanism of action by directly modulating Kv1.5 or $Kv_{(ur)}$. The known class III antiarrythmics ambasilide (Feng et al., 1997), quinidine (Wang et al., 1995), clofilium (Malayev et al., 1995) and bertosamil (Godreau et al., 2002) have all been reported as potassium channel blockers of $Kv_{(ur)}$ in human atrial myocytes. The novel benzopyran derivative, NIP-142, blocks Kv1.5 channels, prolongs the atrial refractory period and terminates atrial fibrillation and flutter in in vivo canine models (Matsuda et al., 2001), and S9947 inhibited Kv1.5 stably expressed in both Xenopus oocytes and Chinese hamster ovary (CHO) cells and $Kv_{(ur)}$ in native rat and human cardiac myocytes (Bachmann et al., 2001). Elsewhere, other novel potassium channel modulators which target Kv1.5 or $Kv_{(ur)}$ have been described for the treatment of cardiac arrhythmias, these include biphenyls (Peukert et al 2003), thiophene carboxylic acid amides (WO0248131), bisaryl derivatives (WO0244137, WO0246162), carbonamide derivatives (WO0100573, WO125189) anthranillic acid amides (WO2002100825, WO02088073, WO02087568), dihydropyrimidines (WO0140231), cycloalkylamine derivatives (WO2005018635), isoquionolines (WO2005030791), quinolines (WO2005030792), imidazopyrazines (WO205034837), benzopyranols (WO2005037780), isoquinolinones (WO2005046578), cycloakyl derivatives (WO03063797), indane derivatives (WO0146155 WO9804521), tetralin benzocycloheptane derivatives (WO9937607), thiazolidone and metathiazanone derivatives (WO9962891), benzamide derivatives (WO0025774), isoquinoline derivatives (WO0224655), pyridazinone derivatives (WO9818475 WO9818476), chroman derivatives (WO9804542), benzopyran derivatives (WO0121610, WO03000675, WO0121609, WO0125224, WO02064581), benzoxazine derivatives (WO0012492), and the novel compound A1998 purified from Ocean material (Xu & Xu, 2000).

Compounds that are undergoing development for atrial fibrillation have recently been reviewed (Page and Rodin, 2005).

Furthermore, the related Kv1.3 channel is expressed in both white and brown adipose tissue, and skeletal muscle (Xu et al., 2004). Inhibition of the channel potentiates the hypoglycemic action of insulin, through increased insulin-stimulated glucose uptake in these tissues. This is supported by in vivo data, showing that Kv1.3 inhibition in mice with type-2 diabetes mellitus were significantly more sensitive to insulin. There is strong evidence that Kv1.3 inhibition improves peripheral glucose metabolism by facilitating GLUT4 translocation to the plasma membrane of adipocytes and myocytes (Desir, 2005). Small molecule inhibitors of Kv1.3 are emerging as potential targets in the management of type-2 diabetes, through their actions as insulin sensitisers (WO02-100248).

Human T-lymphocytes possess two types of potassium channels: the voltage-gated potassium Kv1.3 and the $Ca^{2+}$-activated IKCa1 $K^+$ channels (Leonard et al., 1992, Wulff et al., 2003a). These channels set the resting membrane potential of T-lymphocytes, playing a crucial role in the $Ca^{2+}$ signal transduction pathways that lead to activation of these cells following antigenic stimulation. Disruption of these pathways can attenuate or prevent the response of T-cells to antigenic challenge resulting in immune suppression (Wulff et al., 2004).

The voltage-gated Kv1.3 and the $Ca^{2+}$-activated IKCa1 $K^+$ channels are expressed in T-cells in distinct patterns that accompany the proliferation, maturation and differentiation of these cells. The immunomodulatory effects of channel blockers depends on the expression levels of Kv1.3 and IKCa1 channels, which change dramatically when T-cells transition from resting to activated cells, and during differentiation from the naive to the memory state. Kv1.3 channels dominate functionally in quiescent cells of all T-cell subtypes (naïve, $T_{CM}$ and $T_{EM}$). Activation has diametrically opposite effects on channel expression; as naïve and $T_{CM}$ cells move from resting to proliferating blast cells, they upregulate IKCa1 channels. Consequently activated naïve and $T_{CM}$ cells express ~500 IKCa1 channels and an approximately equivalent number of Kv1.3 channels. In contrast, activation of $T_{EM}$ cells enhances Kv1.3 expression without any change in IKCa1 levels. Functional Kv1.3 expression increases dramatically to 1500 Kv1.3 channels/cell, and their proliferation is sensitive to Kv1.3 blockers (Wulff et al., 2003, Beeton et al., 2003). B-cells also show a switch in $K^+$ channel during differentiation that parallels the changes seen in the T-cell lineage (Wulff et al., 2004). The discovery that the majority of myelin-reactive T-cells in patents with MS are $Kv1.3^{high} T_{EM}$ cells, has raised interest in the therapeutic potential of Kv1.3 blockers in autoimmune disorders (Wulff et al., 2003b, O'Connor et al., 2001). Kv1.3 blockers have been shown to ameliorate adoptive EAE induced by myelin-specific memory T cells (a model for MS) (Beeton et al., 2001) and to prevent inflammatory bone resorption in experimental periodontal disease caused mainly by memory cells (Valverde et al., 2005). In addition, there is increasing evidence implicating late memory cells in the pathogenesis of type-1 diabetes, rheumatoid arthritis, psoriasis, inflammatory bowel disorder, Crohn's disease, chronic graft rejection and chronic graft-vs-host disease (Frierich et al., 2000, Yoon et al., 2001, Viglietta et al., 2002, Yamashita et al., 2004). Specific Kv1.3 blockers might therefore constitute a new class of memory-specific immunomodulators (Shah et al., 2003).

Numerous novel small molecule Kv1.3 channel blockers have been reported for the management of autoimmune disorders. These include the iminodihydroquinolines WIN173173 and CP339818 (Nguyen et al., 1996), the benzhydryl piperidine UK-78,282 (Hanson et al. 1999), correolide (Felix et al., 1999), cyclohexyl-substituted benzamide PAC (US-06194458, WO0025774), sulfamidebenzamidoindane (US-06083986), Khellinone (Baell et al., 2004), dichloropenylpyrazolopyrimidine (WO-00140231) and psoralens (Wulff et al., 1998., Vennekamp et al., 2004, Schmitz et al., 2005).

Thienopyridines have been reported to be useful as antifungal agents, ligand-gated ion-channel modulators, antibacterials and enzyme inhibitors amongst others.

Thienopyridines substituted at the 2- and 3-positions by hydrogen, alkyl, cycloalkyl or aryl groups, at the 4- position by a hydroxyl group, at the 5-position by a carboxy group and by alkyl or aryl substitutents at the nitrogen of the 1-position have been claimed as potent antibacterial agents structurally related to the nalidixic acids (Gilis et al., 1978).

Thienopyridines substituted at the 3-position by a phenyl group, the 2-position by a methyl ketone, the 6-position by a phenyl group, the 5-position by a nitrile group or ester and at the 4-position by an amino group have been claimed as showing antifungal activity against fungi of the family *Aspergillus* and to inhibit mycotoxin production (Abdelrazek et al., 1992).

Thienopyridines substitiuted at the 2-, 3- and 6-positions by alkyl or aryl groups, at the 5-position by an ester, aldehyde or 3,5-dihydroxy heptenoic acid derivative and at the 4-position by a substituted phenyl group have been claimed as potent inhibitors of 3-hydroxy-3-methylglutaryl-coenzyme A (HMG-CoA) Reductase in vitro and to show marked cholesterol biosynthesis inhibitory activities in vivo (Suzuki et al., 2001).

Thienopyridines with a fused cycloalkyl ring between the 5- and 6-positions, and a phenyl group at the 2- and 3-positions have been shown to possess poor inhibitory activity against human acetylcholine esterase (Marco et al., 2002).

Thienopyridines have been claimed as anticancer agents with inhibitory action against the VEGF-2 receptor tyrosine kinase. Claimed compounds include those thienopyridines substituted at the 2-position with alkyl or aromatic moieties, unsubstituted at the 3-position and substituted at the 4-position by an amino group which may be secondary or tertiary and may be directly bound to an aromatic or heterocyclic moiety such as phenyl, indole or benzothiazole (U.S. Pat. No. 6,492,383 B1, Munchof et al., 2004).

Thieno[2,3-b]pyridines with a substituted aniline at the 4-position and a substituted phenyl group at the 2-position have been shown to have modest activity against the Src family of receptor tyrosine kinases as potential anticancer agents. (Boschelli et al, 2004).

Thieno[2,3-b]pyridines with an amino aryl or amino alkyl substituent at the 4-position, an amino group at the 3-position and a carbamoyl substituent at the 2-position have been claimed as modulators of HIV particle formation and Rev-dependant HIV production. (WO2005076861).

Tricyclic 4-amino-5,6,7,8-tetrahydrothieno[2,3-b]quinoline derivatives have been claimed as agents for inhibiting acetylcholinesterase and blocking K+ channels, which is claimed to be useful for activating lowered nerve function induced by senile dementia. (JP04134083).

Thienopyridines with a carbonyl group at the 2-position and an aryl group at the 3-position have been reported as being useful in the treatment of osteoprosis (JP07076586).

4-Amino-7-hydroxy-2-methyl-5,6,7,8-tetrahydrobenzo[b]thieno[2,3-b]pyridine-3-carboxylic acid, but-2-ynyl ester (SB205384) and other tricyclic analogues has been shown to modify the GABA-A receptor modulated chloride current in rat cerebellar granule cells (Meadows et al, 1997).

BRIEF SUMMARY OF THE INVENTION

This invention provides compounds that are potassium channel inhibitors. These compounds are particularly useful for inhibiting one or both of the potassium channels Kv1.5 (or $Kv_{(ur)}$) and Kv1.3. The Kv1.5 channel is a known target for the treatment of cardiac arrhythmia in the atria such as atrial fibrillation (Nattel et al., 1999; Wang et al., 1993); while the Kv1.3 channel is a known target for the treatment of diabetes and immunological disorders. This invention is not limited to the treatment of these disorders, the compounds also being useful to treat other diseases which require potassium channel inhibition (e.g. as described in Shieh et al., 2000; Ford et al., 2002).

DETAILED DESCRIPTION OF THE INVENTION

Thus, in a first aspect, the present invention provides a compound of formula (I).

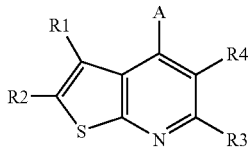

Wherein
R1 is aryl, heteroaryl, cycloalkyl or alkyl;
R2 is H, alkyl, nitro, $CO_2R7$, $CONR5R6$ or halo;
R3, R4 and R5 are H, NR5R6, NC(O)R7, halo, trifluoromethyl, alkyl, CONR5R6, $CO_2R7$, nitrile or alkoxy;
R5 and R6 may be the same or different, and may be H, alkyl, aryl, heteroaryl or cycloalkyl; or R5 and R6 may together form a saturated, unsaturated or partially saturated 4 to 7 member ring, wherein said ring may optionally comprise one or more further heteroatoms selected from N, O or S;
R7 is H, or alkyl;
A is H, halo or a group X-L-Y;
X is O, S or NR8;
R8 is H or alkyl;
L is $(CH_2)_n$, where n is 0, 1, 2, 3 or 4; and
Y is aryl, a heterocyclic group, alkyl, alkenyl or cycloalkyl;
the products of mono- and di-oxidation of sulphur and/or mono-oxidation of nitrogen moieties in compounds of formula I;
or a pharmaceutically acceptable salt thereof;

As used herein, an alkyl group or moiety is typically a linear or branched alkyl group or moiety containing from 1 to 6 carbon atoms, such as a $C_1$-$C_4$ alkyl group or moiety, for example methyl, ethyl, n-propyl, i-propyl, butyl, i-butyl and t-butyl. An alkyl group or moiety may be unsubstituted or substituted at any position. Typically, it is unsubstituted or carries one or two substituents. Suitable substituents include halogen, cyano, nitro, NR9R10, alkoxy, hydroxyl, unsubstituted aryl, unsubstituted heteroaryl, $CO_2R7$, C(O)NR9R10, NC(O)R7 and $SO_2NR9R10$.

As used herein, an aryl group is typically a $C_6$-$C_{10}$ aryl group such as phenyl or napthyl. A preferred aryl group is phenyl. An aryl group may be unsubstituted or substituted at any position. Typically, it carries 1, 2, 3 or 4 substituents. Suitable substituents include cyano, halogen, nitro, trifluoromethyl, alkyl, alkylthio, alkoxy, NR9R10, $CO_2R7$, C(O)NR9R10, NC(O)R7 and $SO_2NR9R10$ and hydroxyl.

As used herein, a heterocyclic group is a heteroaryl group, typically a 5- to 10-membered aromatic ring, such as a 5- or 6-membered ring, containing at least one heteroatom selected from O, S and N. Examples include pyridyl, pyridyl-N-oxide, pyrazinyl, pyrazinyl-N-oxide, pyrimidinyl-N-oxide, pyrimidinyl, pyridazinyl, pyridazinyl-N-oxide, furanyl, thienyl, pyrazolidinyl, pyrrolyl and pyrazolyl groups. Preferred heteroaryl groups are furanyl, thienyl and pyridyl. Examples of polycyclic heterocycles include indolyl, benzofuranyl, benzothiophenyl and benzodioxolyl. Non-aryl heterocyclic groups are also included, such as tetrahydrofuranyl or pyrrolidinyl. A heterocyclic group may be unsubstituted or substituted at any position. Suitable substituents include cyano, nitro, halogen, alkyl, alkylthio, alkoxy, NR9R10, $CO_2R7$, C(O)NR9R10, NC(O)R7 and $SO_2NR9R10$ and hydroxyl.

R9 and R10 can be the same or different, and may be selected from H, unsubstituted alkyl, unsubstituted aryl, unsubstituted heteroaryl, unsubstituted cycloalkyl, aminoethyl, methylaminoethyl, dimethylaminoethyl, hydroxyethyl, alkoxyethyl, or R9 and R10 may together form a saturated, unsaturated or partially saturated 4 to 7 member ring.

When R5 and R6 or R9 and R10 together form a saturated, unsaturated or partially saturated 4 to 7 member ring, the ring may optionally comprise one, two, or three further heteroatoms.

As used herein, alkoxy means $C_{1-3}$ alkoxy, cycloalkyl means $C_{3-6}$ cycloalkyl and halogen means Cl, F, Br, or I, preferably Cl, F or Br.

Compounds of formula I wherein mono- and di-oxidation of sulphur and/or mono-oxidation of nitrogen moieties in the compounds has taken place are also provided. In particular compounds of formula I wherein the thieno[2,3-b]pyridine moiety has been oxidized to one of the following form an embodiment of the invention:
Thieno[2,3-b]pyridine-1-oxide;
Thieno[2,3-b]pyridine-1,1,-dioxide;
Thieno[2,3-b]pyridine-1,1,7,-trioxide;
Thieno[2,3-b]pyridine-1,7,-dioxide; and
Thieno[2,3-b]pyridine-7-oxide.

Preferred compounds of formula I are those wherein R1 is aryl, cycloalkyl or heteroaryl; R2 is H or alkyl; R3 is H, NR5R6, alkoxy or alkyl; X is O or NR8; R8 is H or alkyl; n is 0, 1, 2, 3 or 4 and Y is alkyl, cycloalkyl, aryl or heteroaryl. Particularly preferred compounds of formula I are those wherein R1 is aryl or heteroaryl, R2 is H or alkyl, R3 is H, NR5R6, alkoxy or alkyl, X is O or NR8, R8 is H, n is 0, 1 or 2 and Y is alkyl, cycloalkyl, aryl or heteroaryl.

Preferred compounds include:
(3-Phenyl-thieno[2,3-b]pyridin-4-yl)-pyridin-2-ylmethyl-amine,
2-{3-Phenyl-4-[(pyridin-2-ylmethyl)-amino]-thieno[2,3-b]pyridin-6-ylamino}-ethanol,
2-((2-Hydroxy-ethyl)-{3-phenyl-4-[(pyridin-2-ylmethyl)-amino]-thieno[2,3-b]pyridin-6-yl}-amino)-ethanol,
(6-Chloro-3-phenyl-thieno[2,3-b]pyridin-4-yl)-pyridin-2-ylmethyl-amine,
[3-(4-Fluoro-phenyl)-thieno[2,3-b]pyridin-4-yl]-pyridin-2-ylmethyl-amine,
2-[{3-(4-Fluoro-phenyl)-4-[(pyridin-2-ylmethyl)-amino]-thieno[2,3-b]pyridin-6-yl}-(2-hydroxy-ethyl)-amino]-ethanol,
2-[{3-(4-Fluoro-phenyl)-4-[(6-methyl-pyridin-2-ylmethyl)-amino]-thieno[2,3-b]pyridin-6-yl}-(2-hydroxy-ethyl)-amino]-ethanol,
2-{3-(4-Fluoro-phenyl)-4-[(pyridin-2-ylmethyl)-amino]-thieno[2,3-b]pyridin-6-ylamino}-ethanol,
2-{3-(4-Fluoro-phenyl)-4-[(6-methyl-pyridin-2-ylmethyl)-amino]-thieno[2,3-b]pyridin-6-ylamino}-ethanol,
2-{2-Methyl-3-phenyl-4-[(pyridin-2-ylmethyl)-amino]-thieno[2,3-b]pyridin-6-ylamino}-ethanol,
[6-Chloro-3 -(4-fluoro-phenyl)-thieno[2,3-b]pyridin-4-yl]-pyridin-2-ylmethyl-amine,
[6-Chloro-3 -(4-fluoro-phenyl)-thieno[2,3-b]pyridin-4-yl]-(6-methyl-pyridin-2-ylmethyl)-amine,
[3-(4-Fluoro-phenyl)-thieno[2,3-b]pyridin-4-yl]-(6-methyl-pyridin-2-ylmethyl)-amine,
2-{3-Phenyl-4-[(pyridin-2-ylmethyl)-amino]-thieno[2,3-b]pyridin-6-yl}-propane-1,3-diol, and
(4-Chloro-3-phenyl-thieno[2,3-b]pyridin-6-yl)-pyridin-2-ylmethyl-amine.

In one embodiment of the first aspect of the invention compounds of formula Ia are provided:

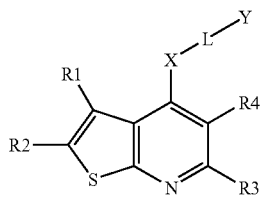

Ia wherein:
R1 is aryl, heteroaryl, cycloalkyl or alkyl;
R2 is H, alkyl, nitro, CO$_2$R7, CONR5R6 or halo;
R3 and R4 are H, NR5R6, NC(O)R7, halo, trifluromethyl, alkyl, CONR5R6, CO$_2$R7, nitrile or alkoxy;
R5 and R6 may be the same or different and may be H, alkyl, aryl, heteroaryl or cycloalkyl; or R5 and R6 may together form a saturated, unsaturated or partially saturated 4 to 7 member ring, wherein said ring may optionally comprise one or more further heteroatoms selected from N, O or S;
R7 is H or alkyl;
X is O, S or NR8;
L is (CH$_2$)$_n$, where n is 1, 2 or 3; and
Y is aryl, a heterocyclic group, alkyl, alkenyl or cycloalkyl;
or a pharmaceutically acceptable salt thereof.
[I have inserted this option, which will clearly be entitled to the claimed priority date. It may provide an option for amendment should there be some relevant intervening priort art, which might be citable against the "new" parts of the subject matter.]

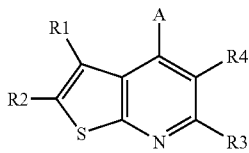

I

Compounds of formula I wherein A is X-L-Y and R3 is NR5R6, nitrile or alkoxy may be synthesised by reaction of compounds of formula II by displacement of the 6-chloro substituent with a suitable nucleophilic species. Such a reaction may be carried out with heating or microwave irradiation optionally in the presence of solvent and a base.

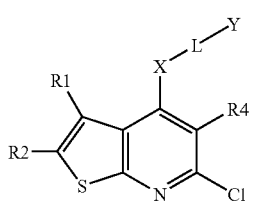

II

Compounds of formula II may be synthesized by reaction of compounds of formula III with a suitable nucleophile X-L-Y, where X, L and Y are as defined herein, optionally in the presence of a solvent and a base, and optionally at elevated temperature or with microwave irradiation. Preferably the solvent is N-methyl pyrrolidinone and the base is a hindered nitrogen base such as triethylamine. If a solvent is present the reaction is carried out at the reflux temperature of the solvent, or under sealed conditions and with microwave irradiation at a temperature of 120-200° C. Also isolable from this reaction is the product of substitution of the 6-chloro substituent.

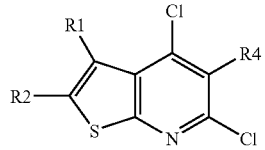

III

Compounds of formula III may be synthesized by reaction of a compound of formula IV with a chlorinating reagent such as phenylphosphonic dichloride or phosphorous oxychloride, optionally in the presence of a suitable solvent.

IV

Compounds of formula IV where R4 is H may be synthesized from compounds of formula V by decarboxylation. This may be performed at elevated temperature, optionally in the presence of a solvent, optionally in the presence of an inorganic base, and optionally with microwave irradiation. If a solvent is present the reaction is carried out at the reflux temperature of the solvent, or under sealed conditions and with microwave irradiation at a temperature of 120-200° C. Preferably the solvent is water or ethanol or an admixture thereof and the base is an inorganic hydroxide preferably sodium or potassium hydroxide.

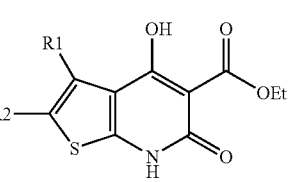

V

Compounds of formula V may be obtained by cyclisation of compounds of formula VI. This may be performed at elevated temperature, preferably in the presence of a solvent, preferably in the presence of an inorganic base, and optionally with microwave irradiation. If a solvent is present the reaction is carried out at the reflux temperature of the solvent, or under sealed conditions and with microwave irradiation at a temperature of 100-150° C. Preferably the solvent is tetrahydrofuran and the base is sodium hydride.

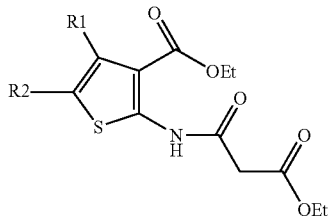

VI

Compounds of formula VI may be synthesized from compounds of formula VII by reaction with diethyl malonate at elevated temperatures or, preferably, with ethyl malonyl chloride in a suitable solvent, preferably dichloromethane, and an organic nitrogen base, preferably triethylamine.

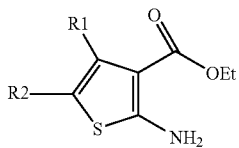

VII

A compound of formula VII can be prepared by reaction of a compound of formula VIII with powdered sulphur, under basic conditions and in a suitable solvent.

Preferably the base is triethylamine and the reaction is carried out at 25 to 65° C. The solvent may be an alcohol, preferably ethanol.

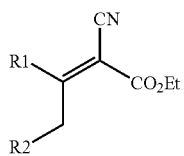

VIII

Compounds of formula VIII can be prepared by heating a compound of formula IX with ethylcyanoacetate ($NCCH_2CO_2Et$) in the presence of an acid and ammonium acetate in a suitable solvent, optionally with azeotropic water removal. Preferably the acid is acetic acid.

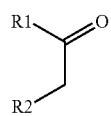

IX

Compounds of formula IX are widely available from commercial sources or can be readily synthesised using standard synthetic organic chemistry procedures.

It is understood that compounds of formula I wherein R3 or R4 is an acid or ester group may undergo functional group transformation using methods familiar to those skilled in the art. In a preferred instance such compounds may undergo amidation by reaction with an alkyl or dialkylamine, or reduction with a reducing agent such as diisobutylaluminium hydride or lithium aluminium hydride.

In an alternative process, particularly applicable to those compounds of formula I wherein R1 is aryl, R2 is H, alkyl or halo, and R3 and R4 are H, a compound of formula X is reacted with a suitable nucleophile X-L-Y, where X, L and Y are as defined herein. Optionally the reaction may be carried out in the presence of a solvent and a base, and optionally at elevated temperature or with microwave irradiation. Preferably the solvent (if present) is an alcohol, preferably ethanol, and the base is a hindered nitrogen base such as triethylamine. If a solvent is present the reaction is carried out at the reflux temperature of the solvent, or under sealed conditions and with microwave irradiation at a temperature of 120-200° C.

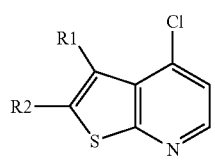

X

A compound of formula X may be obtained from a compound of formula XI by reaction with a chlorinating reagent such as phenylphosphonic dichloride or phosphorous oxychloride (or a mixture thereof) in a suitable solvent or no solvent, and with heating. Preferably the chlorinating reagent is phosphorous oxychloride and the reaction is carried out at reflux temperature and in the absence of additional solvent.

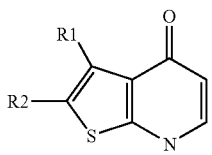

XI

Compounds of formula XI may be obtained by the cyclisation of compounds of formula XII at elevated temperature, optionally in the presence of a solvent, and optionally with microwave irradiation. If a solvent is present the reaction is carried out at the reflux temperature of the solvent, or under sealed conditions and with microwave irradiation at a temperature of 120-200° C. Preferably the solvent is diphenyl ether or Dowtherm and the reaction is carried out at reflux temperature.

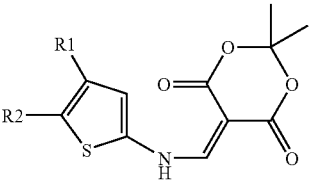

XII

Compounds of formula XII may be obtained from compounds of formula XIII by reaction with Mander's reagent (the condensation product of 2,2-dimethyl-1,3-dioxane-4,6-dione, commonly known as Meldrum's acid, and triethyl orthoformate), at elevated temperature, optionally in the presence of a solvent at a temperature of 50-100° C.

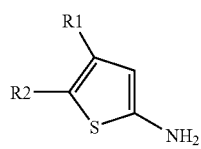

XIII

Compounds of formula XIII may be obtained from compounds of formula VII by decarboxylation. This may be performed at elevated temperature, optionally in the presence of a solvent, optionally in the presence of a base, and optionally with microwave irradiation. If a solvent is present the reaction is carried out at the reflux temperature of the solvent, or under sealed conditions and with microwave irradiation at a temperature of 120-200° C. Preferably the solvent is water or ethanol or an admixture thereof, and the base is an inorganic hydroxide, preferably sodium or potassium hydroxide.

In an alternative synthesis, suitable for compounds of formula I wherein R3 is H, dechlorination of compounds of formula II is carried out. Suitable conditions include the use of zinc powder in acetic acid at a temperature of 80-118° C. This process may also be applied to the side products of reaction of compounds of formula III with nucleophiles, wherein a compound substituted at the 6-position is formed and the remaining 4-chloro substituent removed to provide compounds of formula I wherein A is H.

Alternatively, compounds of formula I wherein R3 is a substituted alkyl group, in a preferred instance an acetic acid ester, can be prepared by the reaction of a compound of formula XIV, where the 4-position of the thienopyridine ring has a suitable leaving group W, by reaction with a suitable nucleophile X-L-Y, where X, L and Y are as defined herein, optionally in the presence of a solvent and a base, and optionally at elevated temperature or with microwave irradiation. Preferably the solvent (if present) is toluene, and the base is a hindered nitrogen base such as triethylamine. In a preferred instance the leaving group W is a halogen, preferably chlorine, or alternatively an alkyl or aryl sulfonate. In a more preferred instance the sulfonate is a trifluoromethanesulfonate. It is understood that compounds of formula I wherein R3 is an acetic acid ester may undergo transformations using methods familiar to those skilled in the art. In a preferred instance, compounds of formula I wherein R3 is a 1-hydroxyethyl group can be prepared by reaction of compounds of formula I wherein R3 is an acetic acid ester with a reducing agent such as diisobutylaluminium hydride or lithium aluminium hydride. In another preferred instance compounds of formula I wherein R3 is a 2-propane-1,3-diol may be obtained by alkylation of compounds of formula I wherein R3 is an acetic acid ester with a dialkyl carbonate or a chloroformate, and reduction of the 1,3-diester formed thereby with a reducing agent such as diisobutylaluminium hydride or lithium aluminium hydride.

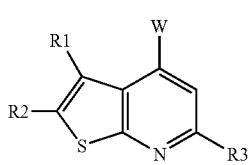

XIV

Compounds of formula XIV wherein W is an alkyl or aryl sulfonate can be obtained from a compound of formula XV by reaction with sulfonating agent, such as a sulfonyl chloride or sulfonic anhydride, in a preferred instance trifluoromethanesulfonic anhydride, in the presence of a solvent and a base, and optionally at elevated temperature or with microwave irradiation. Preferably the solvent is dichloromethane, and the base is a nitrogen base such as pyridine. Compounds of formula XIV wherein W is a halogen, in a preferred instance chlorine, can be obtained from a compound of formula XV by reaction with a chlorinating reagent such as phenylphosphonic dichloride or phosphorous oxychloride (or a mixture thereof) in a suitable solvent or no solvent, and with heating. Preferably the chlorinating reagent is phosphorous oxychloride and the reaction is carried out at reflux temperature and in the absence of additional solvent.

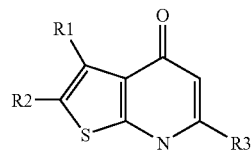

XV

Compounds of formula XV may be obtained from a compound of formula XVI by an intramolecular cyclisation at elevated temperatures. The reaction may involve Lewis acid catalysis such as aluminium trichloride, or mineral acid catalysis such as polyphosphoric acid, optionally in the presence of solvent or as a melt. In a more preferred instance the cyclisation may be induced thermally by heating in a suitable high-boiling solvent, optionally in a microwave. A preferred solvent is diphenyl ether and the reaction is carried out at the reflux temperature of the solvent.

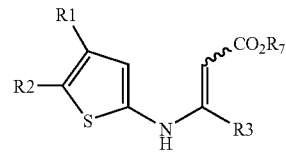

XVI

Compounds of formula XVI may be obtained from compounds of formula XIII by enamine formation with suitably substituted ketones, in a preferred instance diethylacetone dicarboxylate. This reaction may be carried out in the presence of solvent under acid catalysis with removal of water by azeotropic distillation or molecular sieves.

Compounds of formula I wherein A is a halogen group, in particular a chloride substituent, can be isolated as minor products when a compound of formula III is reacted with a nucleophile X-L-Y. It will be understood by those skilled in the art that further manipulation of the chloride substituent in this instance allows the synthesis of those compounds wherein A is hydrogen.

Many of the starting materials referred to in the reactions described above are available from commercial sources or can be made by methods cited in the literature references. Synthetic methods for thienopyridines may be found in references such as Gewald et al (1979), Munchof et al (2004), Barker et al (1985), Charvát et al (1995) and articles cited therein. Synthetic methods can also be found in reviews; thiophenes for example can be found in references cited in Comprehensive Heterocyclic Chemistry, Eds Katritzky, A. R., Rees, C. R., (4), 863-934, and Comprehensive Heterocyclic Chemistry (II), Eds Katritzky, A. R., Rees, C. W., Scriven, E. F. V., (2). 607-678.

Suitable starting materials include:

| Material | Reference | Supplier |
|---|---|---|
| Ethyl Malonyl Chloride | 16,387-2 | Aldrich |
| 4-Fluoroacetophenone | F-320-7 | Aldrich |
| Acetophenone | A1 070-1 | Aldrich |
| 2-(Aminomethyl)pyridine | A6,520-4 | Aldrich |
| Diethanolamine | D8,330-3 | Aldrich |
| ethanolamine | 41,100-0 | Aldrich |
| Propiophenone | P5,160-5 | Aldrich |
| Benzylamine | B1,630-5 | Aldrich |
| 2,2-Dimethyl-1,3-dioxane-4,6-dione | 21,014-5 | Aldrich |
| Triethyl orthoformate | 30,405-0 | Aldrich |
| Diethyl-1,3-Acetone Dicarboxylate | 16,512-3 | Aldrich |

As discussed herein, the compounds of the invention are useful in the treatment of various conditions. Thus, in a second aspect, the present invention provides a compound of formula I or Ia as defined herein for use in medicine. In a further aspect the present invention provides a pharmaceutical formulation comprising at least one compound of formula I or Ia as defined herein and optionally one or more excipients, carriers or diluents.

The compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will depend on the condition being treated, the route of administration and the age, weight and condition of the patient and will be at the doctor's discretion.

The compositions of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

The compounds or compositions of the invention can be used to treat conditions which require inhibition of potassium channels, for example in the treatment of arrythmia. Thus, in further aspects, the present invention provides:

(i) A method of treating or preventing a disorder which requires potassium channel inhibition, eg arrythmia, type-2 diabetes or immunological disorders, comprising administering to a subject an effective amount of at least one compound or pharmaceutical composition of the invention.

(ii) the use of a compound of the invention in the manufacture of a medicament for use in potassium channel inhibition.

In particular, the medicament is for use in the treatment or prevention of arrhythmia, type-2 diabetes and immunological disorders including rheumatoid arthritis, type-1 diabetes, inflammatory bowel disorder and demyelinating disorders such as multiple sclerosis.

EXAMPLES

Using the information outlined herein the following compounds can be synthesised which are given by way of example only. The pharmacological profile of compounds of the present invention can readily be assessed by those skilled in the art using routine experimentation, such as procedures and techniques illustrated herein and described in detail in Ford et al., 2002.

Example 1

2-Cyano-3-phenyl-but-2-enoic Acid Ethyl Ester

A stirred mixture of acetophenone (180 g, 1.5 mol), ethyl cyanoacetate (170 g, 1.3 mol), ammonium acetate (23.1 g), acetic acid (72 g) and toluene (300 ml) was heated under reflux for 18 hours while water was removed from the reaction by azeotropic distillation. The mixture was allowed to cool to ambient temperature, toluene (100 ml) was added, then the mixture was washed with water (3×100 ml). The combined aqueous washings were shaken with toluene (50 ml), then the combined toluene solutions were dried over magnesium sulphate, filtered and the solvent was removed in vacuo. The residual oil was distilled under reduced pressure to give 2-cyano-3-phenyl-but-2-enoic acid ethyl ester as an oil which was used without further purification.

Examples 2 and 3

The compounds set out below were prepared in the same way as in Example 1, using the appropriate starting materials.

| Example | Compound |
| --- | --- |
| 2 | 2-Cyano-3-(4-fluoro-phenyl)-but-2-enoic acid ethyl ester |
| 3 | 2-Cyano-3-phenyl-pent-2-enoic acid ethyl ester |

Example 4

2-Amino-4-phenyl-thiophene-3-carboxylic Acid Ethyl Ester

2-Cyano-3-phenyl-but-2-enoic acid ethyl ester (513.25 g, 2.3 mol) was added at ambient temperature to a vigorously-stirred suspension of powdered sulfur (76 g, 2.3 mol) in ethanol (500 ml). Diethylamine (200 ml) was added in portions over 20 minutes, during which time the temperature of the reaction rose to 62° C. The mixture was allowed to cool to 36° C., then it was heated to 50° C. and stirring at that temperature was continued for 1 hr. After this time, stirring was discontinued, the hot solution was removed by decantation from unreacted sulfur, then it was allowed to cool to ambient temperature. The resulting solid was collected by filtration, washed with a little cold ethanol and dried in vacuo to give 2-amino-4-phenylthiophene-3-carboxylic acid ethyl ester as an orange solid which was used without further purification.

Examples 5 and 6

The compounds set out below were prepared in the same way as in Example 4, using the appropriate starting materials.

| Example | Compound |
| --- | --- |
| 5 | 2-Amino-4-(4-fluoro-phenyl)-thiophene-3-carboxylic acid ethyl ester7 |
| 6 | 2-Amino-5-methyl-4-phenyl-thiophene-3-carboxylic acid ethyl ester |

Example 7

2-(2-Ethoxycarbonyl-acetylamino)-4-phenyl-thiophene-3-carboxylic Acid Ethyl Ester 2-Amino-4-phenyl-thiophene-3-carboxylic acid ethyl ester (5.0 g, 0.02 M) was dissolved in anhydrous dichloromethane (150 ml). Triethylamine (5.56 ml, 0.04 M) was added and the mixture cooled to 0° C. Ethyl Malonyl Chloride (3.79 ml, 0.03 M) was added over 5 min maintaining the temperature at 0° C. The reaction was then stirred at room temperature for 1 hr. Water (100 ml) was added and the organic layer separated. The aqueous layer was extracted with a further 100 ml of dichloromethane. The organics were combined, washed with water (2×100 ml) and dried over sodium sulphate. The concentrated residues were columned on silica, eluting with ethylacetate-cyclohexane 5-10% v/v. Pure fractions were combined and concentrated and the residues triturated with hexane, decanted and dried to give 2-(2-ethoxy-carbonyl-acetylamino)-4-phenyl-thiophene-3-carboxylic acid ethyl ester as a white solid. Yield=6.95 g (96.2%).

Examples 8 and 9

The compounds set out below were prepared in the same way as in Example 7, using the appropriate starting materials.

| Example | Compound |
| --- | --- |
| 8 | 2-(2-Ethoxycarbonyl-acetylamino)-4-(4-fluoro-phenyl)-thiophene-3-carboxylic acid ethyl ester |
| 9 | 2-(2-Ethoxycarbonyl-acetylamino)-5-methyl-4-phenyl-thiophene-3-carboxylic acid ethyl ester |

Example 10

4-Hydroxy-6-oxo-3-phenyl-6,7-dihydro-thieno[2,3-b]pyridine-5-carboxylic Acid Ethyl Ester 2-(2-Ethoxycarbonyl-acetylamino)-4-phenyl-thiophene-3-carboxylic acid ethyl ester (5.0 g, 13.8mmol) and sodium hydride (1.1 g, 27.7 mmol) in anhydrous THF (120 ml) were refluxed for 6 hr under nitrogen. On cooling, solvents were removed in vacuo and the residue suspended in water (100 ml). The mixture was acidified by addition of concentrated hydrochloric acid (5 ml) and stirred for 1 hr. The precipitate was filtered and dried, then recrystallised from ethanol to give 4-hydroxy-6-oxo-3-phenyl-6,7-dihydro-thieno[2,3-b]pyridine-5-carboxylic acid ethyl ester as a pale yellow solid. Yield=2.59 g (63.3%).

Examples 11 and 12

The compounds set out below were prepared in the same way as in Example 10, using the appropriate starting materials.

| Example | Compound |
| --- | --- |
| 11 | 3-(4-Fluoro-phenyl)-4-hydroxy-6-oxo-6,7-dihydro-thieno[2,3-b]pyridine-5-carboxylic acid ethyl ester |
| 12 | 4-Hydroxy-2-methyl-6-oxo-3-phenyl-6,7-dihydro-thieno[2,3-b]pyridine-5-carboxylic acid ethyl ester |

Example 13

4-Hydroxy-3-phenyl-7H-thieno[2,3-b]pyridin-6-one

4-Hydroxy-6-oxo-3-phenyl-6,7-dihydro-thieno[2,3-b]pyridine-5-carboxylic acid ethyl ester (1.5 g, 4.76 mmol) was refluxed in 2 M sodium hydrxide (50 ml) for 5 hr, filtered while still hot, then cooled to 0° C. and acidified to pH 1 by addition of conc. HCl. The resultant white precipitate was filtered and dried to give 4-hydroxy-3-phenyl-7H-thieno[2,3-b]pyridin-6-one as a white solid. Yield=1.05 g (90.7%).

Examples 14 and 15

The compounds set out below were prepared in the same way as in Example 13, using the appropriate starting materials.

| Example | Compound |
| --- | --- |
| 14 | 3-(4-Fluoro-phenyl)-4-hydroxy-7H-thieno[2,3-b]pyridin-6-one |
| 15 | 4-Hydroxy-2-methyl-3-phenyl-7H-thieno[2,3-b]pyridin-6-one |

Example 16

4,6-Dichloro-3-phenyl-thieno[2,3-b]pyridine

A mixture of 4-hydroxy-3-phenyl-7H-thieno[2,3-b]pyridin-6-one (1.05 g, 4.32 mmol) in phenyl phosphonic dichloride (20 ml) was heated to 180° C. for 3 hr. On cooling, the reaction was poured into ice and stirred for 30 min. The aqueous was extracted with DCM (3×100 ml). The extracts were combined, washed with water, dried over sodium sulphate and concentrated. The residue was columned on silica to give 4,6-dichloro-3-phenyl-thieno[2,3-b]pyridine as an opaque oil which slowly crystallised to a pale yellow solid. Yield=0.505 g (42.9%).

Examples 17 and 18

The compounds set out below were prepared in the same way as in Example 16, using the appropriate starting materials.

| Example | Compound |
| --- | --- |
| 17 | 4,6-Dichloro-3-(4-fluoro-phenthieno[2,3-b]pyridine |
| 18 | 4,6-Dichloro-2-methyl-3-phenyl-thieno[2,3-b]pyridine |

Examples 19 and 20

(6-Chloro-3-phenyl-thieno[2,3-b]pyridin-4-yl)-pyridin-2-ylmethyl-amine

A mixture of 4,6-dichloro-3-phenyl-thieno[2,3-b]pyridine (400mg, 1.43mmol) and 2-aminomethylpyridine (294 µl, 1.86 mmol) in NMP (1 ml) were heated in the microwave at 200° C. for 1 h. The reaction was diluted with water (30 ml) and DCM (30 ml). The DCM layer was separated and washed with water (6×50 ml), dried (Na$_2$SO$_4$), and concentrated. The residue was columned on silica, eluting (EtOAc/Hexane 0-100%). The first isolated fraction gave (6-chloro-3-phenyl-thieno[2,3-b]pyridin-4-yl)-pyridin-2-ylmethyl-amine (19) as colourless crystals. Yield=288 mg (57.3%). The second isolated fraction gave (4-Chloro-3-phenyl-thieno[2,3-b]pyridin-6-yl)-pyridin-2-ylmethyl-amine (20) as an orange oil. Yield=24mg (4.7%).

Examples 21 to 23

The compounds set out below were prepared in the same way as in Example 19, using the appropriate starting materials.

| Example | Compound |
| --- | --- |
| 21 | [6-Chloro-3-(4-fluoro-phenyl)-thieno[2,3-b]pyridin-4-yl]-pyridin-2-ylmethyl-amine |
| 22 | [6-Chloro-3-(4-fluoro-phenyl)-thieno[2,3-b]pyridin-4-yl]-(6-methyl-pyridin-2-ylmethyl)-amine |
| 23 | (6-Chloro-2-methyl-3-phenyl-thieno[2,3-b]pyridin-4-yl)-pyridin-2-ylmethyl-amine |

Example 24

2-{3-Phenyl-4-[(pyridin-2-ylmethyl)-amino]-thieno[2,3-b]pyridin-6-ylamino}-ethanol A mixture of (6-chloro-3-phenyl-thieno[2,3-b]pyridin-4-yl)-pyridin-2-ylmethyl-amine (20 mg, 0.57 mmol) and ethanolamine (1 ml) were heated to 200° C. in the microwave and maintained at this temperature for 90 min. On cooling, the reaction mixture was poured into DCM (50 ml) and washed with water (2×50 ml), dried (Na$_2$SO$_4$), and concentrated. The residue was purified on silica (ethyl acetate, 100%) to give 2-{3-phenyl-4-[(pyridin-2-ylmethyl)-amino]-thieno[2,3-b]pyridin-6-ylamino}-ethanol as a white solid. Yield=18 mg (83.9%).

Examples 25 to 30

The compounds set out below were prepared in the same way as in Example 24, using the appropriate starting materials.

| Example | Compound |
|---|---|
| 25 | 2-((2-Hydroxy-ethyl)-{3-phenyl-4-[(pyridin-2-ylmethyl)-amino]-thieno[2,3-b]pyridin-6-yl}-amino)-ethanol |
| 26 | 2-[{3-(4-Fluoro-phenyl)-4-[(pyridin-2-ylmethyl)-amino]-thieno[2,3-b]pyridin-6-yl}-(2-hydroxy-ethyl)-amino]-ethanol |
| 27 | 2-{3-(4-Fluoro-phenyl)-4-[(pyridin-2-ylmethyl)-amino]-thieno[2,3-b]pyridin-6-ylamino}-ethanol |
| 28 | 2-[{3-(4-Fluoro-phenyl)-4-[(6-methyl-pyridin-2-ylmethyl)-amino]-thieno[2,3-b]pyridin-6-yl}-(2-hydroxy-ethyl)-amino]-ethanol |
| 29 | 2-{3-(4-Fluoro-phenyl)-4-[(6-methyl-pyridin-2-ylmethyl)-amino]-thieno[2,3-b]pyridin-6-ylamino}-ethanol |
| 30 | 2-{2-Methyl-3-phenyl-4-[(pyridin-2-ylmethyl)-amino]-thieno[2,3-b]pyridin-6-ylamino}-ethanol |

Example 31

4-Phenyl-thiophen-2-ylamine

2-Amino-4-phenyl-thiophene-3-carboxylic acid ethyl ester (5 g, 20.2 mmol) was suspended in 20% potassium hydroxide solution (100 ml) and heated to reflux. Ethanol (100 ml) was added to aid dissolution. The reaction was stirred overnight and then cooled to room temperature and diluted with water (250 ml). The precipitated solid was collected by filtration and dissolved in DCM/ethyl acetate before drying over magnesium sulfate. The solvent was removed in vacuo to give 4-phenyl-thiophen-2-ylamine. Yield 1.05 g (30%).

Example 32

2,2-Dimethyl-5-[(4-phenyl-thiophen-2-ylamino)-methylene]-[1,3]dioxane-4,6-dione Meldrum's acid (1.05 g, 7.3 mmol) was added to triethyl orthoformate (50 ml) and stirred at 30° C. for 1 hr. The reaction mixture was cooled to room temperature and 4-phenyl-thiophene-2-yl-amine (1.07 g, 6.1 mmol) was added in portions. The reaction mixture was heated to 85° C. and stirred at this temperature overnight before cooling to room temperature. The solvent was removed in vacuo to give a residue which was dissolved in DCM and treated with potassium carbonate. After stirring for 30 min the mixture was filtered and the solvent removed in vacuo to give 2,2-dimethyl-5-[(4-phenyl-thiophen-2-ylamino)-methylene]-[1,3]dioxane-4,6-dione. Yield=1.41 g (70%).

Example 33

3-Phenyl-7H-thieno[2,3-b]pyridine-4-one

Diphenyl ether (15 ml) was heated to reflux and 2,2-dimethyl-5-[(4-phenyl-thiophen-2-ylamino)-methylene]-[1,3]dioxane-4,6-dione (1.41 g, 4.29 mmol) was added in portions with evolution of gas. The reaction mixture was kept at reflux for a further 45 min, before cooling to room temperature. Trituration with diisopropyl ether and petroleum ether (40-60°) gave 3-phenyl-7H-thieno[2,3-b]pyridine-4-one. Yield=0.7 g, (72%).

Example 34

4-Chloro-3-phenyl-thieno[2,3-b]pyridine

3-Phenyl-7H-thieno[2,3-b]pyridine-4-one (0.7 g, 4.29 mmol) was added to phosphorous oxychloride (10 ml) and heated to reflux for 4 hr. The solvent was removed to near dryness and the residue dissolved in DCM. The solution was washed with water followed by saturated sodium hydrogen carbonate and dried over magnesium sulfate. The solution was filtered through a pad of silica and solvents removed in vacuo to give 4-chloro-3-phenyl-thieno[2,3-b]pyridine. Yield=0.261g (25%).

Example 35

(3-Phenyl-thieno[2,3-b]pyridin-4-yl)-pyridin-2-ylmethyl-amine

4-Chloro-3-phenyl-thieno[2,3-b]pyridine (47 mg, 0.19 mmol) and 2-aminomethyl pyridine (0.5 ml, 4.85 mmol) were placed in a 10 ml glass tube. The vessel was sealed with a septum and placed in the microwave cavity. Using microwave irradiation the temperature was ramped from room temperature to 150° C. Once 150° C. was reached, the reaction mixture was held at this temperature for 90 minutes. After cooling to room temperature, the temperature was ramped to 200° C. and held at this temperature for 30 min. After cooling, the reaction mixture was diluted with DCM and washed with water. The organic phase was dried over magnesium sulfate, filtered and concentrated in vacuo. The residue was purified by preparative HPLC to give (3-phenyl-thieno[2,3-b]pyridin-4-yl)-pyridin-2-ylmethyl-amine. Yield=14 mg, 23%.

Example 36

[3-(4-Fluoro-phenyl)-thieno[2,3-b]pyridin-4-yl]-pyridin-2-ylmethyl-amine

[6-Chloro-3-(4-fluoro-phenyl)-thieno[2,3-b]pyridin-4-yl]-pyridin-2-ylmethyl-amine (40 mg, 0.1 mmol) was dissolved in acetic acid (3 ml). Zinc powder (71 mg, 1 mmol) was added and the mixture refluxed for 6 hr. On cooling, the mixture was filtered through celite and the solids washed with further portions of acetic acid (3×5 ml). The acetic acid extracts were neutralized with saturated sodium bicarbonate solution and extracted with DCM (2×50ml). The extracts were combined, dried over sodium sulfate and concentrated. The residue was purified on silica (ethyl actetate/hexane 20-40%) to give [3-(4-fluoro-phenyl)-thieno[2,3-b]pyridin-4-yl]-pyridin-2-ylmethyl-amine as a white solid. Yield=5.5 mg (15.2%).

Example 37

The compound set out below was prepared in the same way as in Example 36, using the appropriate starting materials.

| Example | Compound |
|---------|----------|
| 37 | [3-(4-Fluoro-phenyl)-thieno[2,3-b]pyridin-4-yl]-(6-methyl-pyridin-2-ylmethyl)-amine |

Example 38

(E/Z)-3-(4-Phenyl-thiophen-2-ylamino)-pent-2-enedioic Acid Diethyl Ester

Amino thiophene (1.39 g, 7.94 mmol), p-Toluenesulfonic acid (7.5 mg, 0.4 mmol) and diethylacetonedicarboxylate (1.73 ml, 9.53 mmol) were refluxed for 12 h in chloroform in the presence of 3 Å molecular sieves. On cooling, the reaction was filtered, treated with activated charcoal, refiltered through a pad of celite and concentrated. The residue was triturated with petroleum ether (bp. 40-60°) until crystallisation was complete to give (E/Z)-3-(4-Phenyl-thiophen-2-ylamino)-pent-2-enedioic acid diethyl ester as a brown powder. Yield=2.4g (84%, mixture of E and Z isomers).

Example 39

(4-Oxo-3-phenyl-4,7-dihydro-thieno[2,3-b]pyridin-6-yl)-acetic Acid Ethyl Ester (E/Z)-3-(4-Phenyl-thiophen-2-ylamino)-pent-2-enedioic acid diethyl ester was added portionwise to refluxing Diphenyl ether (20 ml). Once addition was complete, the mixture was refluxed for a further 30 min. On cooling, the reaction was diluted with (bp.40-60° ) petroleum ether (100 ml) and stirred vigorously for 1 h. The initially formed red gum slowly solidified to a fine yellow precipitate. This was filtered, and washed with boiling (bp.40-60°) petroleum ether (2×50 ml) and dried under vacuum to give (4-Oxo-3-phenyl-4,7-dihydro-thieno[2,3-b]pyridin-6-yl)-acetic acid ethyl ester as a yellow powder. Yield=1.89 g, (71%).

Example 40

(3-Phenyl-4-trifluoromethanesulfonyloxy-thieno[2,3-b]pyridin-6-yl)-acetic Acid Ethyl Ester (4-Oxo-3-phenyl-4,7-dihydro-thieno[2,3-b]pyridin-6-yl)-acetic acid ethyl ester (0.8 g, 2.5 mmol), and pyridine (0.2 ml, 2.5 mmol) were dissolved in DCM (5 ml) under nitrogen and cooled to 0° C. Trifluoromethanesulfonic anhydride (0.42 ml, 2.5 mmol) was added dropwise and the reaction stirred for 18 h at room temperature. Solvents were removed in vacuo, and the residue was diluted with water (100 ml) and extracted with DCM (2×50 ml). The extracts were combined, dried over magnesium sulphate, filtered and concentrated to a yellow oil, which solidified on prolonged standing to a waxy yellow solid. This was purified on silica, eluting (DCM/petroleum ether (bp.40-60°)), 0-50%) to give (3-Phenyl-4-trifluoromethanesulfonyloxy-thieno[2,3-b]pyridin-6-yl)-acetic acid ethyl ester as a yellow solid. Yield=878 mg, (78%).

Example 41

{3-Phenyl-4-[(pyridin-2-ylmethyl)-amino]-thieno[2,3-b]pyridin-6-yl}-acetic Acid Ethyl Ester Thienotriflate (Example 40, 0.9 g, 2 mmol), and Hünigs base (0.7 ml, 4 mmol) were dissolved in dry toluene (20 ml) under nitrogen. 2-Aminomethylpyridine (0.2 ml, 2 mmol) was added and the mixture refluxed for 72 h. On cooling, the reaction was washed with water (2×50 ml), dried over magnesium sulfate, filtered and concentrated. The residue was purified on silica, eluting (Ethyl Acetate/petroleum ether (bp.40-60°)), 0-50%) to give {3-Phenyl-4-[(pyridin-2-ylmethyl)-amino]-thieno[2,3-b]pyridin-6-yl}-acetic acid ethyl ester as a yellow solid. Yield=186 mg (26%).

Example 42

2-{3-Phenyl-4-[(pyridin-2-ylmethyl)-amino]-thieno[2,3-b]pyridin-6-yl}-malonic Acid Diethyl Ester {3-Phenyl-4-[(pyridin-2-ylmethyl)-amino]-thieno[2,3-b]pyridin-6-yl}-acetic acid ethyl ester (180 mg, 0.45 mmol) was dissolved in dry THF (10 ml) under nitrogen. Diethyl Carbonate (0.27ml, 2.23 mmol) was added and the mixture cooled to 0° C. Sodium Hydride (36 mg, 0.89 mmol) was added and the mixture stirred at 0° C. for a further 10 min, then at room temperature for 20 min, then brought to reflux for 45 min. On cooling, the reaction was diluted with water (100 ml) and extracted with DCM (3×50 ml), the extracts combined, dried over magnesium sulphate and concentrated. The residue was purified on silica, eluting (Ethyl Acetate/DCM), 0-20%) to give 2-{3-Phenyl-4-[(pyridin-2-ylmethyl)-amino]-thieno[2,3-b]pyridin-6-yl}-malonic acid diethyl ester as a yellow solid. Yield=96 mg (45%).

Example 43

2-{3-Phenyl-4-[(pyridin-2-ylmethyl)-amino]-thieno[2,3-b]pyridin-6-yl}-ethanol

{3-Phenyl-4-[(pyridin-2-ylmethyl)-amino]-thieno[2,3-b]pyridin-6-yl}-acetic acid ethyl ester (47 mg, 0.12 mmol) was dissolved in dry THF (10 ml) under nitrogen and cooled to 0° C. Diisobutyl Aluminium Hydride (0.466 ml of a 1 M solution in hexanes, 0.466 mmol) was added dropwise over 2 min and the mixture stirred at 0° C. for 1 h, then stirred at room temperature overnight. The reaction was cooled to 0° C. and water (5 ml) was added carefully, followed by 1 M Rochelle's salt (5 ml). The reaction was stirred at room temperature for 15 min, and then extracted with DCM (2×25 ml), the extracts combined, dried over magnesium sulphate, and concentrated. The residue was purified on silica, eluting (Ethyl Acetate/Petroleum ether), 50-100%) to give 2-{3-Phenyl-4-[(pyridin-2-ylmethyl)-amino]-thieno[2,3-b]pyridin-6-yl}-ethanol as a brown solid. Yield=25.3 mg (60.4%).

Example 44

2-{3-Phenyl-4-[(pyridin-2-ylmethyl)-amino]-thieno[2,3-b]pyridin-6-yl}-propane-1,3-diol A solution of 2-{3-Phenyl-4-[(pyridin-2-ylmethyl)-amino]-thieno[2,3-b]pyridin-6-yl}-malonic acid diethyl ester (87 mg, 0.18 mmol) in dry THF (10 ml) was cooled to 0° C. under nitrogen. Diisobutyl Aluminium Hydride (1.46 ml of a 1 M solution in hexanes, 1.46 mmol) was added dropwise over 2 min and the mixture stirred at 0° C. for 1 h, then allowed to reach room temperature overnight. The reaction was quenched at 0° C. by adition of 1 M Rochelle's salt (10 ml). The mixture was extracted with DCM (3×20 ml), the extracts combined, washed with brine (50 ml), dried over magnesium sulphate and concentrated. The residue was purified on silica, eluting (Ethyl Acetate, 100%) to give 2-{3-Phenyl-4-[(pyridin-2-ylmethyl)-amino]-thieno[2,3-b]pyridin-6-yl}-propane-1,3-diol_as a yellow oil. Yield=22.5 mg, (31.4%).

Example 45

Analytical Data for compounds representative of the above examples are shown in the table below.

| Example | Compound Name | Mass Spectrum (m/z) |
|---|---|---|
| 7 | 2-(2-Ethoxycarbonyl-acetylamino)-4-phenyl-thiophene-3-carboxylic acid ethyl ester | 7.84 min, 360 (ES−, 100%, [M − H]) |
| 8 | 2-(2-Ethoxycarbonyl-acetylamino)-4-(4-fluoro-phenyl)-thiophene-3-carboxylic acid ethyl ester | 7.80 min, 378 (ES−, 100%, [M − H]) |
| 9 | 2-(2-Ethoxycarbonyl-acetylamino)-5-methyl-4-phenyl-thiophene-3-carboxylic acid ethyl ester | 8.06 min, 374, (ES+, 100%, [M + H]+) |
| 10 | 4-Hydroxy-6-oxo-3-phenyl-6,7-dihydro-thieno[2,3-b]pyridine-5-carboxylic acid ethyl ester | 6.50 min, 316 (ES+, 100%, [M + H]) |
| 11 | 3-(4-Fluoro-phenyl)-4-hydroxy-6-oxo-6,7-dihydro-thieno[2,3-b]pyridine-5-carboxylic acid ethyl ester | 6.51 min, 334 (ES+, 100%, [M + H]) |
| 12 | 4-Hydroxy-2-methyl-6-oxo-3-phenyl-6,7-dihydro-thieno[2,3-b]pyridine-5-carboxylic acid ethyl ester | 6.86 min, 330 (ES+, 100%, [M + H]) |
| 13 | 4-Hydroxy-3-phenyl-7H-thieno[2,3-b]pyridin-6-one | 5.71 min, 244 (ES+, 100%, [M + H]) |
| 14 | 3-(4-Fluoro-phenyl)-4-hydroxy-7H-thieno[2,3-b]pyridin-6-one | 5.75 min, 262 (ES+, 100%, [M + H]) |
| 15 | 4-Hydroxy-2-methyl-3-phenyl-7H-thieno[2,3-b]pyridin-6-one | 5.92 min, 258 (ES+, 100%, [M + H]) |
| 19 | (6-Chloro-3-phenyl-thieno[2,3-b]pyridin-4-yl)-pyridin-2-ylmethyl-amine | 8.00 min, 352 (ES+, 100%, [M + H]) |
| 21 | [6-Chloro-3-(4-fluoro-phenyl)-thieno[2,3-b]pyridin-4-yl]-pyridin-2-ylmethyl-amine | 8.16 min, 370, (ES+, 100%, [M + H]) |
| 22 | [6-Chloro-3-(4-fluoro-phenyl)-thieno[2,3-b]pyridin-4-yl]-(6-methyl-pyridin-2-ylmethyl)-amine | 8.34 min, 384, (ES+, 100%, [M + H]) |
| 23 | (6-Chloro-2-methyl-3-phenyl-thieno[2,3-b]pyridin-4-yl)-pyridin-2-ylmethyl-amine | 8.17 min, 366 (ES+, 100%, [M + H]) |
| 24 | 2-{3-Phenyl-4-[(pyridin-2-ylmethyl)-amino]-thieno[2,3-b]pyridin-6-ylamino}-ethanol | 6.50 min, 377, (ES+, 100%, [M + H]) |
| 25 | 2-((2-Hydroxy-ethyl)-{3-phenyl-4-[(pyridin-2-ylmethyl)-amino]-thieno[2,3-b]pyridin-6-yl}-amino)-ethanol | 6.45 min, 421, (ES+ 100%, [M + H]) |
| 26 | 2-[{3-(4-Fluoro-phenyl)-4-[(pyridin-2-ylmethyl)-amino]-thieno[2,3-b]pyridin-6-yl}-(2-hydroxy-ethyl)-amino]-ethanol | 6.76 min, 439, (ES+ 100%, [M + H]) |
| 27 | 2-{3-(4-Fluoro-phenyl)-4-[(pyridin-2-ylmethyl)-amino]-thieno[2,3-b]pyridin-6-ylamino}-ethanol | 6.75 min, 395, (ES+, 100%, [M + H]) |
| 28 | 2-[{3-(4-Fluoro-phenyl)-4-[(6-methyl-pyridin-2-ylmethyl)-amino]-thieno[2,3-b]pyridin-6-yl}-(2-hydroxy-ethyl)-amino]-ethanol | 6.87 min, 453, (ES+, 100%, [M + H]) |
| 29 | 2-{3-(4-Fluoro-phenyl)-4-[(6-methyl-pyridin-2-ylmethyl)-amino]-thieno[2,3-b]pyridin-6-ylamino}-ethanol | 6.70 min, 409, (ES+, 100%, [M + H]) |
| 30 | 2-{2-Methyl-3-phenyl-4-[(pyridin-2-ylmethyl)-amino]-thieno[2,3-b]pyridin-6-ylamino}-ethanol | 6.83, 391 (ES+, 100%, [M + H]) |
| 36 | [3-(4-Fluoro-phenyl)-thieno [2,3-b]pyridin-4-yl]-pyridin-2-ylmethyl-amine | 7.28 min, 336 (ES+, 100%, [M + H]) |
| 37 | [3-(4-Fluoro-phenyl)-thieno[2,3-b]pyridin-4-yl]-(6-methyl-pyridin-2-ylmethyl)-amine | 7.25 min, 350 (ES+, 100%, [M + H]) |
| 40 | (3-Phenyl-4-trifluoromethanesulfonyloxy-thieno[2,3-b]pyridin-6-yl)-acetic acid ethyl ester | 7.96 min, 446 (ES+, 100%, [M + H]) |
| 41 | {3-Phenyl-4-[(pyridin-2-ylmethyl)-amino]-thieno[2,3-b]pyridin-6-yl}-acetic acid ethyl ester | 7.19 min, 404 (ES+, 100%, [M + H]) |
| 42 | 2-{3-Phenyl-4-[(pyridin-2-ylmethyl)-amino]-thieno[2,3-b]pyridin-6-yl}-malonic acid diethyl ester | 7.59 min, 476 (ES+, 100%, [M + H]) |
| 43 | 2-{3-Phenyl-4-[(pyridin-2-ylmethyl)-amino]-thieno[2,3-b]pyridin-6-yl}-ethanol | 6.35 min, 362 (ES+, 100%, [M + H]) |
| 44 | 2-{3-Phenyl-4-[(pyridin-2-ylmethyl)-amino]-thieno[2,3-b]pyridin-6-yl}-propane-1,3-diol | 6.09 min, 392 (ES+, 100%, [M + H]) |

Example 46

Kv1.3 Autopatch Electrophysiology Method

Cells stably transfected with cDNA for human Kv1.3 were grown in Dulbecco's Modified Eagle media (DMEM) alpha supplemented with 10% Fetal Calf Serum (FCS), 20 µl/ml penicillin (5000 U/ml) streptomycin (5000 µg/ml), 10 µl/ml [100×] glutamine, and blasticidin (7.5 µg/ml). Compounds were tested on these cells using the AutoPatch technology in whole cell mode.

The external bathing solution contained (in mM): 150 NaCl, 10 KCl, 1 $MgCl_2$, 3 $CaCl_2$, 10 HEPES, pH 7.4 with NaOH. Patch pipettes were filled with an electrode solution of composition (in mM): 100 K-Gluconate, 20 KCl, 1 $MgCl_2$, 1 $CaCl_2$, 10 HEPES, 11 EGTA, 5 ATP-$Na_2$, 2 Glutathione pH 7.2 with KOH.

Compounds were dissolved in DMSO (100%) and made up in the external bather at a concentration of 1 µM. All experiments were conducted at room temperature (22-24° C.).

A cell suspension (10 ml), with a density of 100,000 cells/ml, was aliquoted into a 15 ml centrifuge tube and transferred to an incubator (37° C., 5% $CO_2$) for approximately one hour before use. Following 60 min incubation, a tube was taken and centrifuged at 1000 rpm for 4 mins at room temperature. 9.5 ml supernatant was thence discarded, leaving a cell pellet at the bottom of the tube. The pellet was then resuspended using 100 µl of cold (4° C.), filtered (0.22 µm), 0.2% BSA/bather solution (0.02 g BSA/10 ml bather). The bottom of the tube was manually agitated gently until the solution became cloudy with cells. The 100 µl cell resuspension solution was then stored on the bench at 4° C. (using a Peltier-based temperature control device) until used.

A length of capillary glass (1B150F-4, WPI) was dipped into the cell suspension solution, such that ~3 cm column of fluid was taken up by capillary action. A Ag/AgCl wire was dropped into the non-dipped end of the capillary also. The outside of the solution-filled end of the capillary was then dried and the capillary was loaded into the AutoPatch™. Borosilicate glass patch pipettes (from 1.5 mm OD, thin-walled filamented, GC150-TF capillary glass, Harvard) were pulled using a DMZ pipette puller (Zeitz Instruments), and were back-filled using the internal pipette solution, being careful that no bubbles remain at the tip or in the body of the pipette. Patch pipettes typically had resistances of 2.3-3.5 MΩ. Once filled, the pipette tip and a proportion of the shaft (~15mm) were dipped into Sigmacote (Sigma). The recording pipette was then loaded into the AutoPatch™. Automated patch-clamping was initiated by the operator, but thereafter AutoPatch.exe continued the experiment providing that preset conditions and criteria were satisfied.

Whole cell patch-clamp recordings were made using the AutoPatch™ rig, which incorporated an EPC9 or EPC10 amplifier (HEKA, Germany) under control of Pulse software (v8.54 or v8.76, HEKA, Germany), a motion controller with 2 translators (Newport, UK), valve controller (VF1) and a c-level suction device all at room temperature (22-24° C.). This equipment was completely under the control of Auto-Patch.exe and operator intervention was only made when there was a requirement to refill the drug reservoirs or to prevent the loss of a cell due to a technical error. Cells with an $R_{series}$ greater than 18 MΩ were discounted from the experiment.

Qualification stages prior to perfusion and drug application ensured that the observed current met the criteria for the experiment. Only those cells with an $I_K$>400 pA were used for experiments. Cells were continuously perfused with external solution at a flow rate of 1.8-2 ml/minute. The perfusion chamber had a working volume of 80-85 µl and allowed for rapid exchange of drug solutions. Online analysis of the $hK_v1.3$ current during the application of compounds was performed by the AutoPatch™ software. Voltage-step protocols and analysis of data was performed as described for conventional electrophysiology.

Electrophysiology voltage-step protocols and analysis of data was performed as follows. Data was sampled at 5 kHz, and filtered with a −3 dB bandwidth of 2.5 kHz. Cells were held at a voltage of −80 mV. Currents were evoked by a voltage step to +30 mV for 500 ms in duration every 10 s. Currents were analysed using Pulsefit software (v8.54 or v8.76, HEKA, Germany), with the total charge measured during the whole of voltage step. All other plots were produced using Igor Pro (WaveMetrics).

Example 47

Kv1.3 Conventional Whole Cell Patch Electrophysiology Method

Cells stably transfected with cDNA for human Kv1.3 were grown in Dulbecco's Modified Eagle media (DMEM) alpha supplemented with 10% Fetal Calf Serum (FCS), 20 µl/ml penicillin (5000 U/ml) streptomycin (5000 µg/ml), 10 µl/ml [100×] glutamine, and blasticidin (7.5 µg/ml). Compounds were tested on these cells using conventional electrophysiology equipment in whole cell mode.

The external bathing solution contained (in mM): 150 NaCl, 10 Kcl, 1 $MgCl_2$, 3 $CaCl_2$, 10 HEPES, pH 7.4 with NaOH. Patch pipettes were filled with an electrode solution of composition (in mM): 100 K-Gluconate, 20 KCl, 1 $MgCl_2$, 1 $CaCl_2$, 10 HEPES, 11 EGTA, 5 ATP-$Na_2$, 2 Glutathione pH 7.2 with KOH.

Compounds were dissolved in DMSO (100%) and made up in the external bather at a concentration of 1 µM. All experiments were conducted at room temperature (22-24° C.).

Cells were seeded onto 35 mm plastic culture dishes at varying densities and allowed to adhere for at least 4 h before use. Borosilicate glass patch pipettes (from 1.5 mm OD, thin-walled filamented, GC150-TF capillary glass, Harvard) were pulled using a Narishege two stage pipette puller and backed filled with internal solution. Patch pipettes typically had resistances of 3.5-4.5 MΩ.

Whole cell patch-clamp recordings were made using a conventional patch clamp rig, which incorporated an EPC9 or EPC10 amplifier (HEKA, Germany) under control of Pulse software (v8.54 or v8.76, HEKA, Germany. Cells were patched manually and after obtaining the whole cell configuration, drug delivery and experimental parameters were controlled via the AutoPatch™ software. Cells with an $R_{series}$ greater than 18 MΩ were discounted from the experiment.

Qualification stages prior to drug application ensured that the observed current met the criteria for the experiment. Only those cells with an $I_K$>400 pA were used for experiments. Cells were continuously perfused with external solution at a flow rate of 0.5 ml/minute. Online analysis of the $hK_v1.3$ current during the application of compounds was performed by the AutoPatch™ software. Voltage-step protocols and analysis of data was performed using pulsefit (HEKA, Germany).

Electrophysiology voltage-step protocols and analysis of data was performed as follows. Data was sampled at 5 kHz, and filtered with a −3 dB bandwidth of 2.5 kHz.

Cells were held at a voltage of −80 mV. Currents were evoked by a voltage step to +30 mV for 500 ms in duration every 10 s. Currents were analysed using Pulsefit software (v8.54 or v8.76, HEKA, Germany), with the total charge measured during the whole of voltage step. All other plots were produced using Igor Pro (WaveMetrics).

Example 48

Kv1.5 Autopatch Electrophysiology Method

Cells stably transfected with cDNA for human Kv1.5 (in pEF6::VA-His-TOPO) were grown in Dulbecco's Modified Eagle media (DMEM) alpha supplemented with 10% Fetal Calf Serum (FCS), 20 µl/ml penicillin (5000 U/ml) streptomycin (5000 µg/ml), 10 µl/ml [100×] glutamine, and blasticidin (7.5 µg/ml). Compounds were tested on these cells using the AutoPatch technology in whole cell mode.

The external bathing solution contained (in mM): 150 NaCl, 10 KCl, 1 $MgCl_2$, 3 $CaCl_2$, 10 HEPES, pH 7.4 with NaOH. Patch pipettes were filled with an electrode solution of composition (in mM): 160 KCl, 0.5 $MgCl_2$, 10 HEPES, 1 EGTA, pH 7.4 with KOH.

Compounds were dissolved in DMSO (100%) and made up in the external bather at a concentration of 1 µM. All experiments were conducted at room temperature (22-24° C.).

A cell suspension (10 ml), with a density of 100,000 cells/ml, was aliquoted into a 15 ml centrifuge tube and transferred to an incubator (37° C., 5% $CO_2$) for approximately one hour before use. Following 60 min incubation, a tube was taken and centrifuged at 1000 rpm for 4 mins at room temperature. 9.5 ml supernatant was thence discarded, leaving a cell pellet at the bottom of the tube. The pellet was then resuspended using 100 µl of cold (4° C.), filtered (0.22 µm), 0.2% BSA/bather solution (0.02 g BSA/10 ml bather). The bottom of the tube was manually agitated gently until the solution became cloudy with cells. The 100 µl cell resuspension solution was then stored on the bench at 4° C. (using a Peltier-based temperature control device) until used.

A length of capillary glass (1B150F-4, WPI) was dipped into the cell suspension solution, such that ~3 cm column of fluid was taken up by capillary action. A Ag/AgCl wire was dropped into the non-dipped end of the capillary also. The outside of the solution-filled end of the capillary was then dried and the capillary was loaded into the AutoPatch™. Borosilicate glass patch pipettes (from 1.5 mm OD, thin-walled filamented, GC150-TF capillary glass, Harvard) were pulled using a DMZ pipette puller (Zeitz Instruments), and were back-filled using the internal pipette solution, being careful that no bubbles remain at the tip or in the body of the pipette. Patch pipettes typically had resistances of 2.3-3.5 MΩ. Once filled, the pipette tip and a proportion of the shaft (~15 mm) were dipped into Sigmacote (Sigma). The recording pipette was then loaded into the AutoPatch™. Automated patch-clamping was initiated by the operator, but thereafter AutoPatch.exe continued the experiment providing that pre-set conditions and criteria were satisfied.

Whole cell patch-clamp recordings were made using the AutoPatch™ rig, which incorporated an EPC9 or EPC10 amplifier (HEKA, Germany) under control of Pulse software (v8.54 or v8.76, HEKA, Germany), a motion controller with 2 translators (Newport, UK), valve controller (VF1) and a c-level suction device all at room temperature (22-24° C.). This equipment was completely under the control of AutoPatch.exe and operator intervention was only made when there was a requirement to refill the drug reservoirs or to prevent the loss of a cell due to a technical error. Cells with an $R_{series}$ greater than 18 MΩ were discounted from the experiment.

Qualification stages prior to perfusion and drug application ensured that the observed current met the criteria for the experiment. Only those cells with an $I_K$>500 pA were used for experiments. Cells were continuously perfused with external solution at a flow rate of 1.8-2 ml/minute. The perfusion chamber had a working volume of 80-85 µl and allowed for rapid exchange of drug solutions. Online analysis of the $hK_v1.5$ current during the application of compounds was performed by the AutoPatch™ software. Voltage-step protocols and analysis of data was performed as described for conventional electrophysiology.

Electrophysiology voltage-step protocols and analysis of data was performed as follows. Data was sampled at 5kHz, and filtered with a −3 dB bandwidth of 2.5 kHz.

Cells were held at a voltage of −80 mV. Currents were evoked by a voltage step to 0 mV for 1000 ms in duration followed by a step to −40 mV for 1000 ms every 5 s. Currents were analysed using Pulsefit software (v8.54 or v8.76, HEKA, Germany), with the total charge measured during 75-95% of the 0 mV voltage step. All other plots were produced using Igor Pro (WaveMetrics).

Example 49

Kv1.5 Conventional Whole Cell Patch Electrophysiology Method

Cells stably transfected with cDNA for human Kv1.3 were grown in Dulbecco's Modified Eagle media (DMEM) alpha supplemented with 10% Fetal Calf Serum (FCS), 20 µl/ml penicillin (5000 U/ml) streptomycin (5000 µg/ml), 10 µl/ml [100×] glutamine, and blasticidin (7.5 µg/ml). Compounds were tested on these cells using conventional electrophysiology equipment in whole cell mode.

The external bathing solution contained (in mM): 150 NaCl, 10 KCl, 1 $MgCl_2$, 3 $CaCl_2$, 10 HEPES, pH 7.4 with NaOH. Patch pipettes were filled with an electrode solution of composition (in mM): 160 KCl, 0.5 $MgCl_2$, 10 HEPES, 1 EGTA, pH 7.4 with KOH.

Compounds were dissolved in DMSO (100%) and made up in the external bather at a concentration of 1 µM. All experiments were conducted at room temperature (22-24° C.).

Cells were seeded onto 35 mm plastic culture dishes at varying densities and allowed to adhere for at least 4 h before use. Borosilicate glass patch pipettes (from 1.5 mm OD, thin-walled filamented, GC150-TF capillary glass, Harvard) were pulled using a Narishege two stage pipette puller and backed filled with internal solution. Patch pipettes typically had resistances of 3.5-4.5 MΩ.

Whole cell patch-clamp recordings were made using a conventional patch clamp rig, which incorporated an EPC9 or EPC10 amplifier (HEKA, Germany) under control of Pulse software (v8.54 or v8.76, HEKA, Germany. Cells were patched manually and after obtaining the whole cell configuration, drug delivery and experimental parameters were controlled via the AutoPatch™ software. Cells with an $R_{series}$ greater than 18 MΩ were discounted from the experiment.

Qualification stages prior to drug application ensured that the observed current met the criteria for the experiment. Only those cells with an $I_K$>400 pA were used for experiments. Cells were continuously perfused with external solution at a flow rate of 0.5 ml/minute. Online analysis of the $hK_v1.3$ current during the application of compounds was performed by the AutoPatch™ software. Voltage-step protocols and analysis of data was performed using pulsefit (HEKA, Germany).

Electrophysiology voltage-step protocols and analysis of data was performed as follows. Data was sampled at 5 kHz, and filtered with a −3 dB bandwidth of 2.5 kHz. Cells were held at a voltage of −80 mV. Currents were evoked by a voltage step to 0 mV for 1000 ms in duration followed by a step to −40 mV for 1000 ms every 5 s. Currents were analysed using Pulsefit software (v8.54 or v8.76, HEKA, Germany), with the total charge measured during 75-95% of the 0 mV voltage step. All other plots were produced using Igor Pro (WaveMetrics).

Example 50

Representative biological data is presented below:

| Example | Kv1.3 % Inhibition at 1 µM | Kv1.5 % Inhibition at 1 µM |
| --- | --- | --- |
| 24 | 93 | 79 |
| 25 | 82 | 81 |
| 19 | 72 | 88 |
| 20 | 99 | 93 |
| 36 | 32 | 20 |
| 26 | 45 | 91 |
| 28 | 20 | 21 |
| 27 | 72 | 55 |
| 29 | 62 | 31 |
| 21 | 71 | 59 |
| 22 | 78 | 95 |
| 37 | 30 | 36 |
| 35 | 45 | 62 |
| 43 | 20 | 94 |
| 44 | 8 | 82 |

Abbreviations $Kv_{(ur)}$ Cardiac Ultrarapid Delayed Rectifier
CHO Chinese Hamster Ovary Cells
DMEM Dulbecco's Modified Eagle media
FCS Fetal Calf Serum
EBSS Earls Balanced Salt Solution
WCPC Whole-Cell Patch-Clamp
DCM Dichloromethane
NMP N-methylpyrrolidinone
HCL Hydrochloric acid
$Na_2SO_4$ Sodium Sulphate
DME 1,2-Dimethoxyethane
EAE Experimental autoimmune encephalomyelitis
EBSS Earls Balanced Salt Solution
EtOAc Ethyl acetate
EtOH Ethanol
GLUT4 Insulin-regulated glucose transporter
HT Hydroxytryptamine
MgSO4 Magnesium sulfate
MS Multiple sclerosis
$T_{CM}$ Central memory T cell
$T_{EM}$ Effector memory T cell References Herbert, "General principles of the structure of ion channels", Am. J. Med, 104, 87-98, 1998.

Armstrong & Hille, "Voltage-gated ion channels and electrical excitability", Neuron, 20, 371-380, 1998.

Gutman GA et al., International Union of Pharmacology. XLI. Compendium of voltage-gated ion channels: potassium channels. Pharmacol Rev. 2003 Dec; 55(4):583-6.

Shieh et al. "Potassium channels: molecular defects, diseases, and therapeutic opportunities", Pharmacol Rev, 52(4), 557-594, 2000.

Ford et al. "Potassium Channels: Gene Family, Therapeutic Relevance, High-Throughput Screening Technologies and Drug Discovery", Prog Drug Res, 58, 133-168, 2002.

Marban "Cardiac channelopalthies", Nature, 415, 213-218, 213-218, 2002.

Brendel and Peukert 'Blockers of the Kv1.5 Channel for the Treatment of Atrial Arrhythmias', Expert Opinion in Therapeutic Patents, 12 (11), 1589-1598, 2002.

Wang et al., "Sustained depolarization-induced outward current in human atrial myocytes. Evidence for a novel delayed rectifier K+ current similar to Kv1.5 cloned channel currents", Circ Res, 73, 1061-1076, 1993.

Fedida et al., "Identity of a novel delayed rectifier current from human heart with a cloned K+ channel current", Circ Res, 73, 210-216, 1993.

Feng et al., "Antisense oligodeoxynucleotides directed against Kv1.5 mRNA specifically inhibit ultrarapid delayed rectifier K+ current in cultured adult human atrial myocytes", Circ Res, 80, 572-579, 1997.

Amos et al., "Differences between outward currents of human atrial and subepicardial ventricular myocytes", J Physiol, 491, 31-50, 1996.

Li et al., "Evidence for two components of delayed rectifier K+ current in human ventricular myocytes", Circ Res, 78, 689-696, 1996.

Nattel, 'Therapeutic implications of atrial fibrillation mechanisms: can mechanistic insights be used to improve AF management?' Cardiovascular Research, Volume 54, (2), 347-360, 2002.

Courtemanche et al., "Ionic targets for drug therapy and atrial fibrillation-induced electrical remodeling: insights from a mathematical model", Cardiovasc Res, 42(2), 477-489, 1999.

Nattel et al., "Cardiac ultrarapid delayed rectifiers: a novel potassium current family of functional similarity and molecular diversity", Cell Physiol Biochem, 9(4-5), 217-226, 1999.

Knobloch K. et al. Electrophysiological and antiarrhythmic effects of the novel I(Kur) channel blockers, S9947 and S20951, on left vs. right pig atrium in vivo in comparison with the I(Kr) blockers dofetilide, azimilide, d,1-sotalol and ibutilide. Naunyn Schmiedebergs Arch Pharmacol. Nov;366(5): 482-7, 2002.

Wirth KJ et al.,Atrial effects of the novel K(+)-channel-blocker AVE0118 in anesthetized pigs. Cardiovasc Res. Nov 1;60 (2):298-306, 2003.

Colatsky et al., "Channel specificity in antiarrhythmic drug action. Mechanism of potassium channel block and its role in suppressing and aggravating cardiac arrhythmias", Circulation, 82(6), 2235-2242, 1990.

Feng et al., "Effects of class III antiarrhythmic drugs on transient outward and ultra-rapid delayed rectifier currents in human atrial myocytes", J Pharmacol Exp Ther, 281(1), 384-392, 1997.

Wang et al., "Effects of flecainide, quinidine, and 4-aminopyridine on transient outward and ultrarapid delayed rectifier currents in human atrial myocytes", J Pharmacol, 272 (1), 184-196, 1995.

Malayev et al., "Mechanism of clofilium block of the human Kv1.5 delayed rectifier potassium channel", Mol Pharmaco, 147(1), 198-205, 1995.

Godreau et al., "Mechanisms of action of antiarrhythmic agent bertosamil on hKv1.5 channels and outward potassium current in human atrial myocytes", J Pharmacol Exp Ther 300(2), 612-620, 2002.

Matsuda et al., "Inhibition by a novel anti-arrhythmic agent, NIP-142, of cloned human cardiac K+channel Kv1.5 current", Life Sci, 68, 2017-2024, 2001.

Bachmann et al., "Characterization of a novel Kv1.5 channel blocker in Xenopus oocytes, CHO cells, human and rat cardiomyocytes", Naunyn Schmiedebergs Arch Pharmacol, 364(5), 472-478, 2001.

Peukert S, et al., Identification, synthesis, and activity of novel blockers of the voltage-gated potassium channel Kv1.5. J Med Chem. Feb 13;46 (4):486-98, 2003.

Xu & Xu, "The expression of arrhythmic related genes on Xenopus oocytes for evaluation of class III antiarrhythmic drugs from ocean active material", Yi Chuan Xue Bao, 27 (3), 195-201, 2000.

Page and Rodin, 'Drug Therapy for Atrial Fibrillation: Where do we go from here?', Nature Reviews Drug Discovery, 4, 899, 2005.

Xu J et al., "The Voltage-Gated Potassium Channel Kv1.3 Regulates Peripheral Insulin Sensitivity", Proc. Natl. Acad. Sci. USA., 101 (9), 3112-3117, 2004.

Desir GV, "Kv1.3 Potassium Channel Blockade as an Approach to Insulin Resistance", Expert Opin. Ther. Targets, 9 (3), 571-579, 2005.

Leonard et al., "Selective Blockers of Voltage Gated K+ Channels Depolarized Human T Lymphocytes: Mechanism of the Antiproliferative Effects of Charybdotoxin", Proc. Natl. Acad. Sci. USA, 89, 10094, 1992.

Wulff H et al., "Potassium Channels as Therapeutic Targets for Autoimmune Disorders", Curr. Opin. Drg Disov. Dev., 6, 640-647, 2003.

Wulff H et al., "K+ Channel Expression During B Cell Differentiation: Implications for Immunomodulation and Autoimmunity", J Immunol., 173, 776-786, 2004.

Beeton C et al., "A Novel Fluorescent Toxin to Detect and Investigate Kv1.3 Channel Up-regulation in Chronically Activated T Lymphocytes", J. Biol. Chem., 278 (11), 9928-9937, 2003.

Wulff H et al., "The Voltage-gated Kv1.3 K+ Channel in Effector Memory T Cells as New Targets for MS", J. Clin. Invest., 111, 1703-1713, 2003.

O'Connor KC et al., "The Neuroimmunology of Multiple Sclerosis: Possible Roles of T and B Lymphocytes in Immunopathogenesis", J. Clin. Immunol., 21, 81, 2001.

Beeton C et al., "Selective Blockade of T Lymphocyte K+ Channels Ameliorates Experimental Autoimmune Encephalomyelitis, a Model for Multiple Sclerosis", Natl. Acad. Sci. USA, 98 (24), 13942-13947, 2001.

Valverde P et al., "Potassium Channel-blockers as Therapeutic Agents to Interfere with Bone Resorption of Periodontal Disease", J. Dent. Res., 84 (6), 488-499, 2005.

Friedrich M et al., "Flow Cytometric Characterization of Lesional T Cells in Psoriasis: Intracellular Cytokine and Surface Antigen Expression Indicates an Activated, Memory Efector/Type 1 Immunophenotype", Arch. Dermatol. Res., 292, 519, 2000.

Yoon JW et al., "Cellular and Molecular Pathogenic Mechanisms of Insulin-Dependent Diabetes Mellitus", Ann. NY Acad. Sci., 928, 200, 2001.

Viglietta et al., "GAD65-Reactive T Cells are Activated in Patients with Autoimmune Type la Diabetes", J. Clin. Invest., 109, 895, 2002.

Yamashita K et al., "Severe Chronic Graft-versus-host Disease is Characterized by a Preponderance of CD4+ Effector Memory Cells Relative to Central Memory Cells", Blood, 103, 3986-3988, 2004.

Shah K et al., "Immunosuppressive Effects of a Kv1.3 Inhibitor", Cell. Immunol., 221, 100-106, 2003.

Nguyen A et al., "Novel Nonpeptide Agents Potently Block the C-Type Inactivated Conformation of Kv1.3 and Suppress T Cell Activation", Mol. Pharmacol., 50, 1672-1679, 1996.

Hanson DC et al., "UK-78,282, a Novel Piperidine Compound That Potently Blocks the Kv1.3 Voltage-Gated Potassium Channel and Inhibits Human T Cell Activation", Br. J. Pharmacol., 126, 1707-1716, 1999.

Felix JP et al., "Identification and Biochemical Characterization of a Novel Norterpene Inhibitor of the Human Lymphocyte Voltage-Gated Potassium Channel, Kv1.3", Biochemistry, 38 (16), 4922-4930, 1999.

Baell JB et al., "Khellinone Derivatives as Blockers of he Voltage-Gated Potassium Channel Kv1.3: Synthesis and Immunosuppressive Activity" J. Med. Chem., 47, 2326-2336, 2004.

Wulff H et al., "Alkoxypsoralens, Novel Nonpeptide Blockers of Shaker-Type K+ Channels: Synthesis and Photoreactivity", J. Med. Chem., 41, 4542-4549, 1998.

Vennekamp J et al., "Kv1.3-Blocking 5-Phenylalkoxypsoralens: A New Class for Immunomodulators", Mol. Pharmacol., 65, 364-1374, 2004.

Schmitz A et al., "Design of PAP-1, a Selective Small Molecule Kv1.3 Blocker, for the Suppression of Effector Memory T Cells in Autoimmune Diseases", Mol. Pharmacol., 15669, 2005.

Gilis, P.M. et al, Synthesis and antibacterial evaluation of 4, 7-dihydro-4-oxothieno[2,3-b] pyridine-5-carboxylic acids. Eur. J. Med. Chem. Chim. Ther.; 13; 265-269. 1978.

Abdelrazek et al, Synthesis of novel thieno[2,3-d] pyrimidine, thieno[2,3-b]pyridine and thiazolo[3,2-a]thieno[2,3-d] pyrimidine derovatives and their effect on the production of mycotoxins, Arch. Pharm. (Weinheim Ger.); 325 (5) 301-306, 1992.

Suzuki et al, Synthesis and biological evaluations of condensed pyridine and condensed pyrimidine-based HMG-CoA Reductase inhibitors, Bioorg. Med. Chem. Lett; 11 (10); 1285-1288, 2001.

Marco et al, Synthesis and acetylcholesterase/butyrylcholinesterase inhibition activity of of 4-amino-2,3-diaryl-5,6,7, 8-tetrahydrofuro(and thieno)[2,3-b]-quinolines, and 4-amino-5,6,7,8,9-pentahydro-2,3-diphenylcyclohepta[e] furo(and thieno)-[2,3-b] pyridines. Arch. Pharm. (Weinheim Ger.) 335; (7) 347-353, 2002.

Munchof et al., Design and SAR of thienopyrimidine and thienopyridine inhibitors of VEGFR-2 kinase activity. Bioorganic & Medicinal Chemistry Letters, 14 (1), 21-24, 2004.

Barker et al , Thienopyridines Part 6. Synthesis and nucleophilic substitution of some chlorothieno[2,3-b]pyridine derivatives and comparison with the analogous quinoline compounds. J. Chem Res. (Miniprint), 2501-2509, 1998.

Charvát et al., Diethyl Acetonedicarboxylate—a Precursor for the Synthesis of new Substituted 4-Aminoquinolines and Fused 4-Aminopyridines. Monatsheft. Chem. 126, 333-340, 1995.

Gewald et al, Synthesen von 4-Amino-thieno[2,3-b]pyridinen, Monatsheft. Chem. 110, 1189-1196, 1979.

Boschelli et al, Identification of 7-Phenylaminothieno-[3,2-b]pyridine-6-carbonitriles as a New class of Src Kinase Inhibitors, J. Med. Chem. 47, 6666-6668, 2004.

Meadows et al, Effect of SB-205384 on the decay of GABA-activated chloride currents in granule cells cultured from rat cerebellum, British Journal of Pharmacology, 121 (7), 1334-1338, 1997.

Having now fully described this invention, it will be understood by those of ordinary skill in the art that the same can be performed with a wide and equivalent range of conditions, formulations, and other parameters without affecting the scope of the invention or any embodiment thereof All patents and publications cited herein are fully incorporated by reference herein in their entireties.

What is claimed is:

1. A compound of the formula:

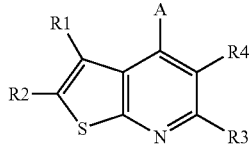

I wherein

R1 is optionally substituted aryl, optionally substituted heteroaryl, or optionally substituted cycloalkyl;

R2 is H, optionally substituted alkyl, nitro, $CO_2R7$, CONR5R6 or halo;

R3 and R4 are H, NR5R6, NC(O)R7, halo, trifluoromethyl, optionally substituted alkyl, CONR5R6, $CO_2R7$, cyano or optionally substituted alkoxy;

R5 and R6 may be the same or different and may be H, optionally substituted alkyl, optionally substituted aryl, optionally substituted heteroaryl or optionally substituted cycloalkyl; or R5 and R6 may together form a saturated, unsaturated or partially saturated 4 to 7 member ring, wherein said ring may optionally comprise one or more further heteroatoms selected from N, O or S;

R7 is H or optionally substituted alkyl;

A is halo, or a group of formula X-L-Y;

X is O, S or NR8;

R8 is H or optionally substituted alkyl;

L is $(CH_2)_n$, where n is 1, 2, 3 or 4; and

Y is optionally substituted aryl, an optionally substituted heterocyclic group, optionally substituted alkyl, optionally substituted alkenyl or optionally substituted cycloalkyl;

or a pharmaceutically acceptable salt thereof.

2. The compound as claimed in claim 1, or a pharmaceutically acceptable salt thereof, wherein R1 is optionally substituted aryl, optionally substituted cycloalkyl or optionally substituted heteroaryl; R2 is H or optionally substituted alkyl; R3 is H, NR5R6, optionally substituted alkoxy or optionally substituted alkyl; X is O or NR8; R8 is H or optionally substituted alkyl; n is 1, 2, 3 or 4 and Y is optionally substituted alkyl, optionally substituted cycloalkyl, optionally substituted aryl or optionally substituted heteroaryl.

3. The compound as claimed in claim 2, or a pharmaceutically acceptable salt thereof, wherein R1 is optionally substituted aryl or optionally substituted heteroaryl; R2 is H or optionally substituted alkyl; R3 is H, NR5R6, optionally substituted alkoxy or optionally substituted alkyl; X is NR8; R8 is H or methyl; n is 1 or 2 and Y is optionally substituted aryl or optionally substituted heteroaryl.

4. The compound as claimed in claim 3 which is:

(3-Phenyl-thieno[2,3-b]pyridin-4-yl)-pyridin-2-ylmethyl-amine,

2-{3-Phenyl-4-[(pyridin-2-ylmethyl)-amino]-thieno[2,3-b]pyridin-6-ylamino}-ethanol, 2-((2-Hydroxy-ethyl)-{3-phenyl-4-[(pyridin-2-ylmethyl)-amino]-thieno[2,3-b]pyridin-6-yl}-amino)-ethanol, (6-Chloro-3-phenyl-thieno[2,3-b]pyridin-4-yl)-pyridin-2-ylmethyl-amine,

[3-(4-Fluoro-phenyl)-thieno[2,3-b]pyridin-4-yl]-pyridin-2-ylmethyl-amine,

2-[{3-(4-Fluoro-phenyl)-4-[(pyridin-2-ylmethyl)-amino]-thieno[2,3-b]pyridin-6-yl}-(2-hydroxy-ethyl)-amino]-ethanol, 2-[{(3-(4-Fluoro-phenyl)-4-[(6-methyl-pyridin-2-ylmethyl)-amino]-thieno[2,3-b]pyridin-6-yl}-(2-hydroxy-ethyl)-amino]-ethanol, 2-{3-(4-Fluoro-phenyl)-4-[(pyridin-2-ylmethyl)-amino]-thieno[2,3-b]pyridin-6-ylamino}-ethanol, 2-{3-(4-Fluoro-phenyl)-4-[(6-methyl-pyridin-2-ylmethyl)-amino]-thieno[2,3-b]pyridin-6-ylamino}-ethanol, 2-{2-Methyl-3-phenyl-4-[(pyridin-2-ylmethyl)-amino]-thieno[2,3-b]pyridin-6-ylamino}-ethanol,

[6-Chloro-3-(4-fluoro-phenyl)-thieno[2,3-b]pyridin-4-yl]-pyridin-2-ylmethyl-amine,

[6-Chloro-3-(4-fluoro-phenyl)-thieno[2,3-b]pyridin-4-yl]-(6-methyl-pyridin-2-ylmethyl)-amine,

[3-(4-Fluoro-phenyl)-thieno[2,3-b]pyridin-4-yl]-(6-methyl-pyridin-2-ylmethyl)-amine, 2-{3-Phenyl-4-[(pyridin-2-ylmethyl)-amino]-thieno[2,3-b]pyridin-6-yl}-propane-1,3-diol, or (4-Chloro-3-phenyl-thieno[2,3-b]pyridin-6-yl)-pyridin-2-ylmethyl-amine;

or a pharmaceutically acceptable salt thereof.

5. A compound of the formula:

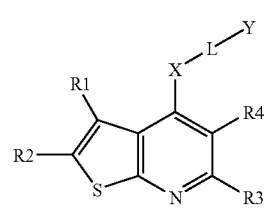

Ia wherein:

R1 is optionally substituted aryl, optionally substituted heteroaryl, optionally substituted cycloalkyl or optionally substituted alkyl;

R2 is H, optionally substituted alkyl, nitro, $CO_2R7$, CONR5R6 or halo;

R3 and R4 are H, NR5R6, NC(O)R7, halo, trifluoromethyl, optionally substituted alkyl, CONR5R6, $CO_2R7$, cyano or optionally substituted alkoxy;

R5 and R6 may be the same or different and may be H, optionally substituted alkyl, optionally substituted aryl, optionally substituted heteroaryl or optionally substituted cycloalkyl; or R5 and R6 may together form a saturated, unsaturated or partially saturated 4 to 7 member ring, wherein said ring may optionally comprise one or more further heteroatoms selected from N, O or S;

R7 is H or optionally substituted alkyl;

X is O, S or NR8;

R8 is H or optionally substituted alkyl;

L is (CH$_2$)$_n$, where n is 1, 2 or 3; and

Y is optionally substituted aryl, an optionally substituted heterocyclic group, optionally substituted alkyl, optionally substituted alkenyl or optionally substituted cycloalkyl;

or a pharmaceutically acceptable salt thereof.

6. A pharmaceutical composition comprising at least one compound of claim 1.

7. The pharmaceutical composition according to claim 6 further comprising one or more pharmaceutically acceptable excipients, diluents, carriers, and mixtures thereof.

8. A pharmaceutical composition comprising at least one compound of claim 3.

9. A pharmaceutical composition comprising at least one compound of claim 5.

10. The pharmaceutical composition according to claim 8 further comprising one or more pharmaceutically acceptable excipients, diluents, carriers, and mixtures thereof.

* * * * *